United States Patent
Sutcliffe et al.

(10) Patent No.: US 6,555,569 B2
(45) Date of Patent: Apr. 29, 2003

(54) USE OF HETEROARYL SUBSTITUTED N-(INDOLE-2-CARBONYL-) AMIDES FOR TREATMENT OF INFECTION

(75) Inventors: Joyce A. Sutcliffe, Clinton, CT (US); Judith Lee Treadway, Mystic, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/785,146

(22) Filed: Feb. 16, 2001

(65) Prior Publication Data

US 2001/0046985 A1 Nov. 29, 2001

Related U.S. Application Data

(60) Provisional application No. 60/187,605, filed on Mar. 7, 2000.

(51) Int. Cl.[7] .................. A61K 31/405; A61K 31/40; A61K 31/47; A61K 31/445; A61K 31/395
(52) U.S. Cl. .................. 514/415; 514/419; 514/311; 514/314; 514/315; 514/317; 514/326; 514/330; 514/210.19; 514/210.2
(58) Field of Search .................. 514/210, 325, 514/414, 419, 415, 311, 314, 317, 326, 330, 210.19, 210.2, 315

(56) References Cited

U.S. PATENT DOCUMENTS 6,235,285 B1     5/2001     Burnham

FOREIGN PATENT DOCUMENTS

| EP | 0894861 | 3/1999 | |
|----|---------|--------|----|
| WO | WO 96/39384 A1 * | 12/1996 | .......... C07D/209/42 |
| WO | WO 96/39385 A1 * | 12/1996 | .......... C07D/209/42 |

OTHER PUBLICATIONS

Berkow, R., The Merck Manual of Diagnosis and Therapy (16th ED) (1992).*

Berrs et al., The Merck Manual of Diagnosis and Therapy (17th ED) (1999).*

Martin et al., *Discovery of a human liver glycogen phosphorylase inhibitor that lowers blood glucose in vivo*, Proc. Natl. Acad. Sci. USA, vol. 95, pp. 1776–1781, Feb. 1998.

Letter from Prof. Dr. W. Goebel to Dr. Judith Treadway dated Mar. 25, 1998.

* cited by examiner

*Primary Examiner*—Sreeni Padmanabhan
*Assistant Examiner*—S. Jiang
(74) *Attorney, Agent, or Firm*—Peter C. Richardson; Gregg C. Benson; Seth H. Jacobs

(57) ABSTRACT

A pharmaceutical composition containing a glycogen phosphorylase inhibitor of Formula I or IA as defined herein is administered to a mammal to treat infection.

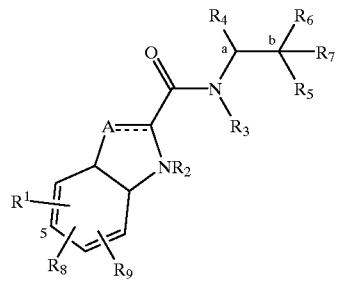

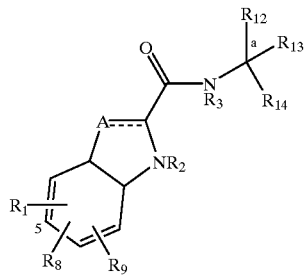

7 Claims, No Drawings

USE OF HETEROARYL SUBSTITUTED N-(INDOLE-2-CARBONYL-) AMIDES FOR TREATMENT OF INFECTION

This application claims priority under 35 U.S.C. § 119(e) of U.S. application Ser. No. 60/187,605, filed Mar. 7, 2000, which application is hereby incorporated by reference herein.

FIELD OF THE INVENTION

This invention relates to the use of certain glycogen phosphorylase inhibitors in the treatment of infections.

BACKGROUND OF THE INVENTION

Glycogenolysis in tissues, whereby glycogen is cleaved to release glucose-1-phosphate, is catalyzed by glycogen phosphorylase (GP). In humans, three isoforms of this enzyme have been identified: the liver isoform (HLGP), the muscle isoform (HMGP), and the brain isoform (HBGP). These isoforms are products of three separate genes and have 80–83% amino acid identity (C. B. Newgard, D. R. Littman, C. van Gendered, M. Smith, and R. J. Fletterick, J. Biol. Chem.263:3850–3857, 1988). Glycogen phosphorylase is also present in bacteria.

Glycogen phosphorylase inhibitors that have been reported to date include glucose and glucose analogs (e.g., Martin, J. L. et al., Biochemistry 1991, 30, 10101), caffeine and other purine analogs (e.g., Kasvinsky, P. J. et al. J. Biol. Chem. 1978, 253, 3343–3351 and 9102–9106), and inhibitors of the type described by Oikonomakos, N. G. et al., Protein Sci. 1999, 8, 1930–1945.

Glycogen phosphorylase inhibitors are useful in the treatment of diabetes mellitus. For example, International Patent publications WO 96139384 and WO 96/39385, both published Dec. 12, 1996, describe use of substituted N-(indole-2-carbonyl-) amides and derivatives for treatment of diabetes. These compounds are also described as useful in treatment of atherosclerosis, hyperinsulinemia, hypercholesterolemia, hypertension, hyperlipidemia, and in prevention of myocardial ischemic injury.

U.S. Pat. No. 5,952,322 describes the use of glycogen phosphorylase inhibitors, such as those described in WO 96/39384 and WO 96/39385, to reduce tissue damage associated with non-cardiac ischemia.

U.S. Pat. No. 5,882,885, issued Mar. 16, 1999 refers to antagonists and agonists of streptococcal glycogen phosphorylase as useful in the treatment of otitis media, conjunctivitis, pneumonia, bacteremia, meningitis, sinusitis, pleural empyema and endocarditis.

SUMMARY OF THE INVENTION

The present invention relates to a method of treating or preventing infection, e.g., bacterial, fungal, parasitic, or viral infection, comprising administering an amount of a compound of Formula I or Formula IA that is effective in treating or preventing said infection.

Compounds of the Formula I and Formula IA have the following structures:

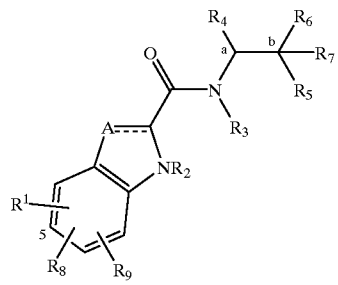

Formula I

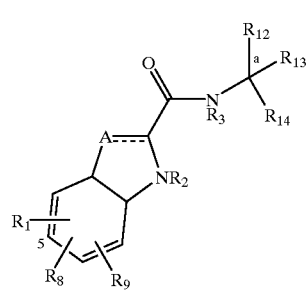

Formula IA and the pharmaceutically acceptable salts and prodrugs thereof;

wherein:

the dotted line (---) is an optional bond;

A is —C(H)=, —C((C$_1$–C$_4$)alkyl)= or —C(halo)= when the dotted line (---) is a bond, or A is methylene or —CH((C$_1$–C$_4$)alkyl)— when the dotted line (---) is not a bond;

R$_1$, R$_8$ or R$_9$ are each independently H, halo, 4-, 6- or 7-nitro, cyano, (C$_1$–C$_4$)alkyl, (C$_1$–C$_4$)alkoxy, fluoromethyl, difluoromethyl or trifluoromethyl;

R$_2$ is H;

R$_3$ is H or (C$_1$–C$_5$)alkyl;

R$_4$ is H, methyl, ethyl, n-propyl, hydroxy(C$_1$–C$_3$)alkyl, (C$_1$–C$_3$)alkoxy(C$_1$–C$_3$)alkyl, phenyl(C$_1$–C$_4$)alkyl, phenylhydroxy(C$_1$–C$_4$)alkyl, phenyl(C$_1$–C$_4$)alkoxy (C$_1$–C$_4$)alkyl, thien-2- or -3-yl(C$_1$–C$_4$)alkyl or fur-2- or -3-yl(C$_1$–C$_4$)alkyl wherein said R$_4$ rings are mono-, di- or tri-substituted independently on carbon with H, halo, (C$_1$–C$_4$)alkyl, (C$_1$–C$_4$)alkoxy, trifluoromethyl, hydroxy, amino or cyano; or R$_4$ is pyrid-2-, -3- or -4-yl(C$_1$–C$_4$)alkyl, thiazol-2-, -4- or -5-yl(C$_1$–C$_4$)alkyl, imidazol -1-, -2-, -4- or -5-yl (C$_1$–C$_4$)alkyl, pyrrol-2- or -3-yl(C$_1$–C$_4$)alkyl, oxazol-2-, -4- or -5-yl-(C$_1$–C$_4$)alkyl pyrazol-3-, -4- or -5-yl (C$_1$–C$_4$)alkyl, isoxazol-3-, -4- or -5-yl(C$_1$–C$_4$)alkyl, isothiazol-3-, -4- or -5-yl(C$_1$–C$_4$)alkyl, pyridazin-3- or -4-yl-(C$_1$–C$_4$)alkyl, pyrimidin-2-, -4-, -5- or -6-yl (C$_1$–C$_4$)alkyl, pyrazin-2- or -3-yl(C$_1$–C$_4$)alkyl or 1,3,5-triazin-2-yl(C$_1$–C$_4$)alkyl, wherein said preceding R$_4$ heterocycles are optionally mono- or di-substituted independently with halo, trifluoromethyl, (C$_1$–C$_4$) alkyl, (C$_1$–C$_4$)alkoxy, amino or hydroxy and said mono-or di-substituents are bonded to carbon;

R$_5$ is H, hydroxy, fluoro, (C$_1$–C$_5$)alkyl, (C$_1$–C$_5$)alkoxy, (C$_1$–C$_6$)alkanoyl, amino(C$_1$–C$_4$)alkoxy, mono-N- or di-N,N-(C$_1$–C$_4$)alkylamino(C$_1$–C$_4$)alkoxy, carboxy (C$_1$–C$_4$)alkoxy, (C$_1$–C$_5$)alkoxy-carbonyl(C$_1$–C$_4$)

alkoxy, benzyloxycarbonyl($C_1$–$C_4$)alkoxy, or carbonyloxy wherein said carbonyloxy is carbon-carbon linked with phenyl, thiazolyl, imidazolyl, 1H-indolyl, furyl, pyrrolyl, oxazolyl, pyrazolyl, isoxazolyl, isothiazolyl, pyridazinyl, pyrimidinyl, pyrazinyl or 1,3,5-triazinyl and wherein said preceding $R_5$ rings are optionally mono-substituted with halo, ($C_1$–$C_4$)alkyl, ($C_1$–$C_4$)alkoxy, hydroxy, amino or trifluoromethyl and said mono-substituents are bonded to carbon;

$R_7$ is H, fluoro or ($C_1$–$C_5$)alkyl; or $R_5$ and $R_7$ can be taken together to be oxo;

$R_6$ is C(O)$R_{10}$;

$R_{10}$ is piperazin-1-yl, 4-($C_1$–$C_4$)alkylpiperazin-1-yl, 4-formylpiperazin-1-yl, morpholino, thiomorpholino, 1-oxothiomorpholino, 1,1-dioxo-thiomorpholino, thiazolidin-3-yl, 1-oxo-thiazolidin-3-yl, 1,1-dioxothiazolidin-3-yl, 2-($C_1$–$C_6$)alkoxycarbonylpyrrolidin-1-yl, oxazolidin-3-yl or 2(R)-hydroxymethylpyrrolidin-1-yl; or $R_{10}$ is 3- and/or 4-mono-or di-substituted oxazetidin-2-yl, 2-, 4-, and/or 5- mono- or di-substituted oxazolidin-3-yl, 2-, 4-, and/or 5- mono- or di- substituted thiazolidin-3-yl, 2-, 4-, and/or 5- mono- or di- substituted 1-oxothiazolidin-3-yl, 2-, 4-, and/or 5- mono- or di-substituted 1,1-dioxothiazolidin-3-yl, 3- and/or 4-, mono- or di-substituted pyrrolidin-1-yl, 3-, 4-and/or 5-, mono-, di- or tri-substituted piperidin-1-yl, 3-, 4-, and/or 5- mono-, di-, or tri-substituted piperazin-1-yl, 3-substituted azetidin-1-yl, 4- and/or 5-, mono- or di-substituted 1,2-oxazinan-2-yl, 3-and/or 4-mono- or di-substituted pyrazolidin-1-yl, 4- and/or 5-, mono- or di-substituted isoxazolidin-2-yl, 4- and/or 5-, mono-and/or di-substituted isothiazolidin-2-yl wherein said $R_{10}$ substituents are independently H, halo, ($C_1$–$C_5$)-alkyl, hydroxy, amino, mono-N- or di-N,N-($C_1$–$C_5$)alkylamino, formyl, oxo, hydroxyimino, ($C_1$–$C_5$)alkoxy, carboxy, carbamoyl, mono-N-or di-N,N-($C_1$–$C_4$)alkylcarbamoyl, ($C_1$–$C_4$)alkoxyimino, ($C_1$–$C_4$)alkoxymethoxy, ($C_1$–$C_6$)alkoxycarbonyl, carboxy($C_1$–$C_5$)alkyl or hydroxy($C_1$–$C_5$)alkyl;

$R_{12}$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, (phenyl)(($C_1$–$C_4$)-alkoxy)($C_1$–$C_4$)alkyl, thien-2- or -3-yl($C_1$–$C_4$)alkyl or fur-2- or -3-yl($C_1$–$C_4$)alkyl wherein said $R_{12}$ rings are mono-, di- or tri-substituted independently on carbon with H, halo, ($C_1$–$C_4$)alkyl, ($C_1$–$C_4$)alkoxy, trifluoromethyl, hydroxy, amino, cyano or 4,5-dihydro-1H-imidazol-2-yl; or $R_{12}$ is pyrid-2-, -3- or -4-yl($C_1$–$C_4$)alkyl, thiazol-2-, -4- or -5-yl($C_1$–$C_4$)alkyl, imidazol-2-, -4- or -5-yl($C_1$–$C_4$)alkyl, pyrrol-2- or -3-yl($C_1$–$C_4$)alkyl, oxazol-2-, -4- or -5-yl($C_1$–$C_4$)alkyl, pyrazol-3-, -4- or -5-yl($C_1$–$C_4$)alkyl, isoxazol-3-, -4- or -5-yl($C_1$–$C_4$)alkyl, isothiazol-3-, 4- or -5-yl($C_1$–$C_4$)alkyl, pyridazin-3- or -4-yl($C_1$–$C_4$)alkyl, pyrimidin-2-, -4-, -5- or -6-yl($C_1$–$C_4$)alkyl, pyrazin-2-or - 3-yl($C_1$–$C_4$)alkyl, 1,3,5-triazin-2-yl($C_1$–$C_4$)alkyl or indol-2-($C_1$–$C_4$)alkyl, wherein said preceding $R_{12}$ heterocycles are optionally mono- or di-substituted independently with halo, trifluoromethyl, ($C_1$–$C_4$)alkyl, ($C_1$–$C_4$)alkoxy, amino, hydroxy or cyano and said substituents are bonded to carbon; or $R_{12}$ is $R_{11}$-carbonyloxymethyl, wherein said $R_{11}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{11}$ rings are optionally mono- or di-substituted independently with halo, amino, hydroxy, ($C_1$–$C_4$)alkyl, ($C_1$–$C_4$)alkoxy or trifluoromethyl and said mono- or di-substituents are bonded to carbon;

$R_{13}$ is H, methyl, ethyl, n-propyl, hydroxymethyl, or hydroxyethyl;

$R_{14}$ C(O)$R_{15}$;

$R_{15}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4-dihydroisoquinolin-2-yl, 1,3-dihydroisoindol-2-yl, 3,4-dihydro-2H-quinol-1 -yl, 2,3-dihydro-benzo[1, 4]oxazin4-yl, 2,3-dihydro-benzo[1,4]-thiazine-4-yl, 3,4-dihydro-2H-quinoxalin-1 -yl, 3,4-dihydrobenzo[c][1,2]oxazin-1-yl, 1,4-dihydro-benzo[d][1,2]oxazin-3-yl, 3,4-dihydro-benzo[e][1,2]-oxazin-2-yl, 3H-benzo[d]isoxazol-2-yl, 3H-benzo[c]isoxazol-1-yl or azepan-1-yl, wherein said $R_{15}$ rings are optionally mono-, di- or tri-substituted independently with halo, ($C_1$–$C_5$)alkyl, ($C_1$–$C_5$)alkoxy, hydroxy, amino, mono-N- or di-N,N-($C_1$–$C_5$)alkylamino, formyl, carboxy, carbamoyl, mono-N- or di-N,N-($C_1$–$C_5$)alkylcarbamoyl, ($C_1$–$C_6$)alkoxy($C_1$–$C_3$)alkoxy, ($C_1$–$C_5$)alkoxycarbonyl, benzyloxycarbonyl, ($C_1$–$C_5$)alkoxycarbonyl($C_1$–$C_5$)alkyl, ($C_1$–$C_4$)alkoxycarbonylamino, carboxy($C_1$–$C_5$)alkyl, carbamoyl($C_1$–$C_5$)alkyl, mono-N- or di-N,N-($C_1$–$C_5$)alkylcarbamoyl($C_1$–$C_5$)alkyl, hydroxy($C_1$–C5)alkyl, ($C_1$–$C_4$)alkoxy($C_1$–$C_4$)alkyl, amino($C_1$–$C_4$)alkyl, mono-N- or di-N,N-($C_1$–$C_4$)alkylamino($C_1$–$C_4$)alkyl, oxo, hydroxyimino or ($C_1$–$C_6$)alkoxyimino and wherein no more than two substituents are selected from oxo, hydroxyimino or ($C_1$–$C_6$)alkoxyimino and oxo, hydroxyimino or ($C_1$–$C_6$)alkoxyimino are on nonaromatic carbon; and wherein said $R_{15}$ rings are optionally additionally mono- or di-substituted independently with ($C_1$–$C_5$)alkyl or halo.

A group of preferred compounds of Formula I consists of those compounds wherein:

$R_1$ is 5-H, 5-halo, 5-methyl or 5-cyano;

$R_8$ and $R_9$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di- substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol -1-, -2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, 4- or -5-yl-($C_1$–$C_2$)alkyl, pyrazol-3-, -4- or -5-yl ($C_1$–$C_2$)alkyl, isoxazol-3-, 4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is hydroxy; and $R_7$is H.

Within the above group of preferred compounds of Formula I is a second group of especially preferred compounds wherein the carbon atom labelled a has (S) stereochemistry;

the carbon atom labelled b has (R) stereochemistry;

$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro; and $R_{10}$ is morpholino, 4-($C_1$–$C_4$)alkylpiperazin-1-yl, 3-substituted azetidin-1-yl, 3- and/or 4-, mono- or di-substituted pyrrolidin-1-yl, 4- and/or 5- mono- or di-substituted isoxazolidin-2-yl, 4- and/or 5-, mono- or di-substituted 1,2-oxazinan-2-yl wherein said substituents are each independently H, halo, hydroxy, amino, mono-N- or di-N,N-($C_1$–$C_6$)alkylamino, oxo, hydroxyimino or alkoxy.

Within the above group of especially preferred compounds are the particularly preferred compounds:

5-Chloro-1H-indole-2-carboxylic acid [(1S)-benzyl-(2R)-hydroxy-3-(4-methylpiperazin-1-yl)-3-oxo-propyl]-amide hydrochloride, 5-Chloro-1H-indole-2-carboxylic acid [(1S)-benzyl-(2R)-hydroxy-3-(3-hydroxyazetidin-1-yl)-3-oxo-propyl]-amide, 5-Chloro-1H-indole-2-carboxylic acid ((1S)-benzyl-(2R)-hydroxy-3-isoxazolidin-2-yl-3-oxo-propyl)-amide, 5-Chloro-1H-indole-2-carboxylic acid ((1S)-benzyl-(2R)-hydroxy-3-[1,2]oxazinan-2-yl-3-oxo-propyl)-amide, 5-Chloro-1H-indole-2-carboxylic acid [(1S)-benzyl-(2R)-hydroxy-3-((3S)-hydroxypyrrolidin-1-yl)-3-oxo-propyl]-amide, 5-Chloro-1H-indole-2-carboxylic acid [(1S)-benzyl-3-((3S,4S)-dihydroxy-pyrrolidin-1-yl)-(2R)-hydroxy-3-oxo-propyl]-amide, 5-Chloro-1H-indole-2-carboxylic acid [(1S)-benzyl-3-(cis-3,4-dihydroxy-pyrrolidin-1-yl)-(2R)-hydroxy-3-oxo-propyl]-amide; and 5-Chloro-1H-indole-2-carboxylic acid ((1S)-benzyl-(2R)-hydroxy-3-morpholin-4-yl-3-oxo-propyl)-amide.

Within the above group of especially preferred compounds of Formula I are compounds wherein:

a.
- $R_1$ is 5-chloro;
- $R_8$ and $R_9$ are H;
- $R_4$ is benzyl; and
- $R_{10}$ is 4-methylpiperazin-1-yl;

b.
- $R_1$ is 5-chloro;
- $R_8$ and $R_9$ are H;
- $R_4$ is benzyl; and
- $R_{10}$ is 3-hydroxyazetidin-1-yl;

c.
- $R_1$ is 5-chloro;
- $R_8$ and $R_9$ are H;
- $R_4$ is benzyl; and
- $R_{10}$ is isoxazolidin-2-yl;

d.
- $R_1$ is 5-chloro;
- $R_8$ and $R_9$ are H;
- $R_4$ is benzyl; and
- $R_{10}$ is (1,2)-oxazinan-2-yl;

e.
- $R_1$ is 5-chloro;
- $R_8$ and $R_9$ are H;
- $R_4$ is benzyl; and
- $R_{10}$ is 3(S)-hydroxypyrrolidin-1-yl;

f.
- $R_1$ is 5-chloro;
- $R_8$ and $R_9$ are H;
- $R_4$ is benzyl; and
- $R_{10}$ is (3S,4S)-dihydroxypyrrolidin-1-yl;

g.
- $R_1$ is 5-chloro;
- $R_8$ and $R_9$ are H;
- $R_4$ is benzyl; and
- $R_{10}$ is cis-3,4-dihydroxypyrrolidin-1-yl; and h.
- $R_1$ is 5-chloro;
- $R_8$ and $R_9$ are H;
- $R_4$ is benzyl; and
- $R_{10}$ is morpholino.

Another group of preferred compounds of Formula I are those wherein:

$R_1$ is H, halo, methyl or cyano;

$R_8$ and $R_9$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di- substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol -1-, -2-, -4- or -5-yl($C_1$–$C_2$)aikyl, fur-2- or -3-yl ($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is fluoro, ($C_1$–$C_4$)alkyl, ($C_1$–$C_5$)alkoxy, amino($C_1$–$C_4$) alkoxy, mono-N- or di-N,N-($C_1$–$C_4$)alkylamino ($C_1$–$C_4$)alkoxy, carboxy($C_1$–$C_4$)alkoxy, ($C_1$–$C_5$) alkoxy-carbonyl($C_1$–$C_4$)alkoxy, benzyloxycarbonyl ($C_1$–$C_4$)alkoxy; and $R_7$ is H, fluoro or ($C_1$–$C_6$)alkyl.

A group of preferred compounds of Formula IA consists of those compounds wherein:

$R_1$ is 5-H, 5-halo, 5-methyl, 5-cyano or 5-trifluoromethyl;

$R_8$ and $R_9$ are each independently H or halo;

A is —C(H)=;

$R_2$ and $R_3$ are H;

$R_{12}$ is H, methyl, phenyl($C_1$–$C_2$)alkyl, wherein said phenyl groups are mono- or di-substituted independently with H, halo, ($C_1$–$C_4$)alkyl, ($C_1$–$C_4$)alkoxy, trifluoromethyl, hydroxy, amino or cyano and wherein said $R_{12}$ groups are optionally additionally mono-substituted with halo; or $R_{12}$ is thien-2- or -3-yl($C_1$–$C_2$)alkyl, pyrid-2-, -3- or -4-yl($C_1$–$C_2$)alkyl, thiazol-2-, -4- or -5-yl($C_1$–$C_2$)alkyl, imidazol-2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl, isothiazol-3-, -4- or -5-yl($C_1$–$C_2$)alkyl, pyridazin-3- or -4-yl($C_1$–$C_2$)alkyl, pyrimidin-2-, -4-, -5- or -6-yl($C_1$–$C_2$)alkyl, pyrazin-2- or -3-yl($C_1$–$C_2$)alkyl or 1,3,5-triazin-2-yl($C_1$–$C_2$)alkyl wherein said preceding $R_{12}$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon; and $R_{13}$ is H.

Within the above group of preferred compounds of Formula IA is a group of especially preferred compounds wherein:

$R_{12}$ is H, phenyl($C_1$–$C_2$)alkyl, thien-2- or -3-yl($C_1$–$C_2$)alkyl, fur-2- or -3-yl($C_1$–$C_2$)alkyl wherein said $R_{12}$ rings are mono- or di-substituted independently with H or fluoro; and $R_{15}$ is morpholino, thiomorpholino, 1-oxothiomorpholino, 1,1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, isothiazolidin-2-yl, 1,2-oxazetidin-2-yl, oxazolidin-3-yl, 1,3-dihydroisoindol-2-yl, or azepan-1-yl, wherein said $R_{15}$ rings are optionally mono- or di-substituted independently with halo, ($C_1$–$C_5$)alkyl, ($C_1$–$C_5$)alkoxy, hydroxy, amino, mono-N-or di-N,N-($C_1$–$C_5$)alkylamino, formyl, carboxy, carbamoyl, mono-N- or di-N,N-($C_1$–$C_5$)alkylcarbamoyl, ($C_1$–$C_5$)alkoxycarbonyl, hydroxy($C_1$–$C_5$)alkyl, amino($C_1$–$C_4$)alkyl, mono-N- or di-N,N-($C_1$–$C_4$)alkylamino($C_1$–$C_4$)alkyl, oxo, hydroxyimino or ($C_1$–$C_6$)alkoxyimino with the proviso that only the $R_{15}$ heterocycles thiazolidin-3-yl, pyrrolidin-1-yl, piperidin-1-yl, piperazin-1-yl, piperazin-4-yl, azetidin-1-yl, 1,2-oxazinan-2-yl, isoxazolidin-2-yl, or oxazolidin-3-yl are optionally mono- or di-substituted with oxo, hydroxyimino, or ($C_1$–$C_6$)alkoxyimino; and wherein said $R_{15}$ rings are optionally additionally mono- or di-substituted independently with ($C_1$–$C_5$)alkyl.

Within the above group of especially preferred compounds are the compounds:

5-Chloro-1H-indole-2-carboxylic acid [(1S)-benzyl-2-(3-hydroxyimino-pyrrolidin-1-yl)-2-oxo-ethyl]-amide, 5-Chloro-1H-indole-2-carboxylic acid [2-(cis-3,4-dihydroxy-pyrrolidin-1-yl)-2-oxo-ethyl]-amide, 5-Chloro-1H-indole-2-carboxylic acid [2-((3S,4S)-dihydroxy-pyrrolidin-1-yl)-2-oxo-ethyl]-amide, 5-Chloro-1H-indole-2-carboxylic acid [(1S)-benzyl-2-(cis-3,4-dihydroxy-pyrrolidin-1-yl)-2-oxo-ethyl]-amide, 5-Chloro-1H-indole-2-carboxylic acid [2-(1,1-dioxo-thiazolidin-3-yl)-2-oxo-ethyl]-amide, 5-Chloro-1H-indole-2-carboxylic acid (2-oxo-2-thiazolidin-3-yl-ethyl)-amide, 5-Chloro-1H-indole-2-carboxylic acid [(1S)-(4-fluoro-benzyl)-2-(4-hydroxy-piperidin-1-yl)-2-oxo-ethyl]-amide, 5-Chloro-1H-indole-2-carboxylic acid [(1S)-benzyl-2-((3RS)-hydroxy-piperidin-1-yl)-2-oxo-ethyl]-amide, 5-Chloro-1H-indole-2-carboxylic acid [2-oxo-2-((1RS)-oxo-1-thiazolidin-3-yl)-ethyl]-amide, 5-Chloro-1H-indole-2-carboxylic acid [(1S)-(2-fluoro-benzyl)-2-(4-hydroxy-piperidin-1-yl)-2-oxo-ethyl]-amide, 5-Chloro-1H-indole-2-carboxylic acid [(1S)-benzyl-2-((3S,4S)-dihydroxy-pyrrolidin-1-yl)-2-oxo-ethyl]-amide, 5-Chloro-1H-indole-2-carboxylic acid [(1S)-benzyl-2-(3-hydroxy-azetidin-1-yl)-2-oxo-ethyl]-amide, 5-Chloro-1H-indole-2-carboxylic acid [(1S)-benzyl-2-(3-hydroxyimino-azetidin-1-yl)-2-oxo-ethyl]-amide, 5-Chloro-1H-indole-2-carboxylic acid [(1S)-benzyl-2-(4-hydroxyimino-piperidin-1-yl)-2-oxo-ethyl]-amide, and 5-Chloro-1H-indole-2-carboxylic acid [1-benzyl-2-(3-hydroxypyrrolidin-1-yl)-2-oxo-ethyl]amide.

Within the above group of especially preferred compounds of Formula IA is a group of particularly preferred compounds wherein:

$R_{12}$ is H; and $R_{15}$ is thiazolidin-3-yl, 1-oxo-thiazolidin-3-yl, 1,1-dioxothiazolidin-3-yl or oxazolidin-3-yl or said $R_{15}$ substituents optionally mono- or di-substituted independently with carboxy, ($C_1$–$C_5$)alkoxycarbonyl, hydroxy ($C_1$–$C_3$)alkyl, amino($C_1$–$C_3$)alkyl, mono-N- or di-N,N-($C_1$–$C_3$)alkylamino($C_1$–$C_3$)alkyl or $R_{15}$ is mono- or di-substituted pyrrolidin-1-yl wherein said substituents are independently carboxy, ($C_1$–$C_5$)alkoxycarbonyl, ($C_1$–$C_5$)alkoxy, hydroxy, hydroxy($C_1$–$C_3$)alkyl, amino, amino($C_1$–$C_3$)alkyl, mono-N- or di-N,N-($C_1$–$C_3$)alkylamino($C_1$–$C_3$)alkyl or mono-N- or di-N,N-($C_1$–$C_4$)alkylamino; and the $R_{15}$ rings are optionally additionally independently disubstituted with ($C_1$–$C_5$)alkyl.

Preferred compounds within the immediately preceding group of compounds are those wherein:

a.
$R_1$ is 5-chloro;
$R_8$ and $R_9$ are H; and
$R_{15}$ is cis-3,4-dihydroxy-pyrrolidin-1-yl;

b.
$R_1$ is 5-chloro;
$R_8$ and $R_9$ are H; and
$R_{15}$ is (3S,4S)-dihydroxy-pyrrolidin-1-yl;

c.
$R_1$ is 5-chloro;
$R_8$ and $R_9$ are H; and
$R_{15}$ is 1,1-dioxo-thiazolidin-3-yl;

d.
$R_1$ is 5-chloro;
$R_8$ and $R_9$ are H; and
$R_{15}$ is thiazolidin-3-yl; and e.
$R_1$ is 5-chloro;
$R_8$ and $R_9$ are H; and
$R_{15}$ is 1-oxo-thiazolidin-3-yl.

Within the above group of especially preferred compounds of Formula IA is another group of particularly preferred compounds wherein:

$R_{15}$ is phenylmethyl, thien-2- or -3-ylmethyl wherein said $R_{15}$ rings are optionally mono- or di-substituted with fluoro; and $R_{15}$ is thiazolidin-3-yl, 1-oxo-thiazolidin-3-yl, 1,1-dioxothiazolidin-3-yl or oxazolidin-3-yl or said $R_{15}$ substituents optionally mono- or di-substituted independently with carboxy or ($C_1$–$C_5$)alkoxycarbonyl, hydroxy ($C_1$–$C_3$)alkyl, amino($C_1$–$C_3$)alkyl or mono-N- or di-N,N-($C_1$–$C_3$)alkylamino($C_1$–$C_3$)alkyl or $R_{15}$ is mono- or di-substituted azetidin-1-yl or mono- or di-substituted pyrrolidin-1-yl or mono- or di-substituted piperidin-1-yl wherein said substituents are independently carboxy, ($C_1$–$C_5$)alkoxycarbonyl, hydroxy($C_1$–$C_3$)alkyl, amino($C_1$–$C_3$)alkyl, mono-N- or di-N,N-($C_1$–$C_3$)alkylamino($C_1$–$C_3$)alkyl, hydroxy, ($C_1$–$C_5$)alkoxy, amino, mono-N- or di-N,N-($C_1$–$C_5$) alkylamino, oxo, hydroxyimino or ($C_1$–$C_5$) alkoxyimino; and the $R_{15}$ rings are optionally additionally mono- or di-substituted independently with ($C_1$–$C_5$)alkyl.

Preferred compounds within the immediately preceding group of particularly preferred compounds of Formula IA are compounds wherein a.
- $R_1$ is 5-chloro;
- $R_8$ and $R_9$ are H;
- $R_{12}$ is 4-fluorobenzyl;
- $R_{15}$ is 4-hydroxypiperidin-1-yl; and
- the stereochemistry of carbon (a) is (S);

b.
- $R_1$ is 5-chloro;
- $R_8$ and $R_9$ are H;
- $R_{12}$ is benzyl;
- $R_{15}$ is 3-hydroxypiperidin-1-yl; and
- the stereochemistry of carbon (a) is (S);

c.
- $R_1$ is 5-chloro;
- $R_8$ and $R_9$ are H;
- $R_{12}$ is benzyl;
- $R_{15}$ is cis-3,4-dihydroxy-pyrrolidin-1-yl; and
- the stereochemistry of carbon (a) is S;

d.
- $R_1$ is 5-chloro;
- $R_8$ and $R_9$ are H; $R_{12}$ is benzyl;
- $R_{15}$ is 3-hydroxyimino-pyrrolidin-1-yl; and
- the stereochemistry of carbon (a) is (S);

e.
- $R_1$ is 5-chloro;
- $R_8$ and $R_9$ are H;
- $R_{12}$ is 2-fluorobenzyl;
- $R_{15}$ is 4-hydroxypiperidin-1-yl; and
- the stereochemistry of carbon (a) is (S);

f.
- $R_1$ is 5-chloro;
- $R_8$ and $R_9$ are H;
- $R_{12}$ is benzyl;
- $R_{15}$ is (3S,4S)-dihydroxy-pyrrolidin-1-yl; and
- the stereochemistry of carbon (a) is (S);

g.
- $R_1$ is 5-chloro;
- $R_8$ and $R_9$ are H;
- $R_{12}$ is benzyl;
- $R_{15}$ is 3-hydroxy-azetidin-1-yl; and
- the stereochemistry of carbon (a) is (S);

h.
- $R_1$ is 5-chloro;
- $R_8$ and $R_9$ are H;
- $R_{12}$ is benzyl;
- $R_{15}$ is 3-hydroxyimino-azetidin-1-yl; and
- the stereochemistry of carbon (a) is (S); and i.
- $R_1$ is 5-chloro;
- $R_8$ and $R_9$ are H;
- $R_{12}$ is benzyl;
- $R_{15}$ is 4-hydroxyimino-piperidin-1-yl; and
- the stereochemistry of carbon (a) is (S).

The glycogen phosphorylase inhibitor of formula I or IA is employed to treat bacterial infections and protozoa infections and disorders related to such infections that include the following: pneumonia, otitis media, sinusitus, bronchitis, tonsillitis, and mastoiditis related to infection by *Streptococcus pneumoniae, Haemophilus influenzae, Moraxella catarrhalis, Staphylococcus aureus*, or Peptostreptococcus spp.; pharynigitis, rheumatic fever, and glomerulonephritis related to infection by *Streptococcus pyogenes*, Groups C and G streptococci, *Clostridium diptheriae*, or *Actinobacillus haemolyticum*; respiratory tract infections related to infection by *Mycoplasma pneumoniae, Legionella pneumophila, Streptococcus pneumoniae, Haemophilus influenzae*, or *Chlamydia pneumoniae*; uncomplicated skin and soft tissue infections, abscesses and osteomyelitis, and puerperal fever related to infection by *Staphylococcus aureus*, coagulase-positive staphylococci (i.e., *S. epidermidis, S. hemolyticus*, etc.), *Streptococcus pyogenes, Streptococcus agalactiae*, Streptococcal groups C–F (minute-colony streptococci), viridans streptococci, *Corynebacterium minutissimum*, Clostridium spp., or *Bartonella henselae*; uncomplicated acute urinary tract infections related to infection by *Staphylococcus saprophyticus* or Enterococcus spp.; urethritis and cervicitis; and sexually transmitted diseases related to infection by *Chlamydia trachomatis, Haemophilus ducreyi, Treponema pallidum, Ureaplasma urealyticum*, or *Neiserria gonorrheae*; toxin diseases related to infection by *S. aureus* (food poisoning and Toxic shock syndrome), or Groups A, B, and C streptococci; ulcers related to infection by *Helicobacter pylori*; systemic febrile syndromes related to infection by *Borrelia recurrentis*; Lyme disease related to infection by *Borrelia burgdorferi*; conjunctivitis, keratitis, and dacrocystitis related to infection by *Chlamydia trachomatis, Neisseria gonorrhoeae, S. aureus, S. pneumoniae, S. pyogenes*, or *H. influenzae*; disseminated *Mycobacterium avium* complex (MAC) disease related to infection by *Mycobacterium avium*, or *Mycobacterium intracellulare*; gastroenteritis related to infection by *Campylobacter jejuni*; intestinal protozoa related to infection by Cryptosporidium spp.; odontogenic infection related to infection by viridans streptococci; persistent cough related to infection by *Bordetella pertussis*; gas gangrene related to infection by *Clostridium perfringens* or Bacteroides spp.; atherosclerosis related to infection by *Helicobacter pylori, Chlamydia pneumoniae*, or *Mycoplasma pneumoniae*, dysentery related to infection by *Shigella dysenteriae*, and symptoms of infection by enterotoxigenic *E. coli* or *Mycobacterium tuberculosis*. Bacterial infections and protozoa infections and disorders related to such infections that may be treated or prevented in animals include the following: bovine respiratory disease related to infection by *Pasteurella haemolyticus, P. multocida, Mycoplasma bovis*, or Bordetella spp.; cow enteric disease related to infection by *E. coli* or protozoa (i.e., coccidia, cryptosporidia, etc.); dairy cow mastitis related to infection by *Staph. aureus, Strep. uberis, Strep. agalactiae, Strep. dysgalactiae*, Klebsiella spp., Corynebacterium, or Enterococcus spp.; swine respiratory disease related to infection by *Actinobaciflus pleuropneumoniae, P. multocida*, or Mycoplasma spp.; swine enteric disease related to infection by *E. coli, Lawsonia intracellularis*, Salmonella, or *Serpulina hyodysenteriae*; cow footrot related to infection by Fusobacterium spp.; cow metritis related to infection by *E. coli*; cow hairy warts related to infection by *Fusobacterium* necrophorum or Bacteroides nodosus; cow pink-eye related to infection by Moraxella bovis; cow premature abortion related to infection by protozoa (i.e. neosporium); urinary tract infection in dogs and cats related to infection by E. coli; skin and soft tissue infections in dogs and cats related to infection by Staph. epidermidis, Staph intermedius, coagulase neg. Staph. or P. multocida; and dental or mouth infections in dogs and cats related to infection by Alcaligenes spp., Bacteroides spp., Clostridium spp., Enterobacter spp., Eubacterium, Peptostreptococcus, Porphyromonas, or Prevotella. The invention also encompasses treatment of bacteremia, meningitis, pleural empyema, malaria, river blindness, toxoplasmosis, and endocarditis. Other bacterial infections and protozoa infections and disorders related to such infections that may be treated or prevented in accord with the method of the present invention are referred to in J. P. Sanford et al., "The Sanford Guide To Antimicrobial Therapy," 26th Edition, (Antimicrobial Therapy, Inc., 1996).

In one embodiment, the infection that is treated according to the invention is mediated by an organism that requires glycogen, or glucose that results from the breakdown of glycogen, as a source of energy and/or carbon supply.

In another embodiment, the glycogen phosphorylase inhibitor is administered in an amount that reduces or eliminates infection sufficiently to reduce complications, including long-term complications, that can be associated with the infection. These complications include, but are not limited to asthma, and cerebrovascular disease.

In an alternative embodiment, the present invention relates to a pharmaceutical composition for the treatment of bacterial infection comprising an amount of a compound of Formula I or IA effective to treat said infection in combination with a pharmaceutically acceptable carrier.

In another embodiment, a glycogen phosphorylase inhibitor is administered to treat Chiamydia pneumoniae infection.

DETAILED DESCRIPTION OF THE INVENTION

All patents, patent publications, and literature references cited herein are hereby incorporated by reference.

It is intended that reference to particular compounds herein be interpreted to mean that the pharmaceutically acceptable anionic or cationic salts and prodrugs of those compounds may also be employed.

Methods for making the glycogen phosphorylase inhibitors described herein are described in detail in U.S. Pat. No. 5,952,322 and in WO 96/39384 and WO 96/39385.

The term glycogen phosphorylase inhibitor refers to a substance or agent or combination of substances and/or agents which reduces, retards, or eliminates the enzymatic action of glycogen phosphorylase. The currently known enzymatic action of glycogen phosphorylase is the degradation of glycogen by catalysis of the reversible reaction of a glycogen macromolecule and inorganic phosphate to glucose-1-phosphate and a glycogen macromolecule which is one glucosyl residue shorter than the original glycogen macromolecule (forward direction of glycogenolysis).

The term "treating" as used herein includes preventative (e.g., prophylactic) and palliative treatment.

By halo is meant chloro, bromo, iodo, or fluoro.

By alkyl is meant straight chain or branched saturated hydrocarbon. Exemplary of such alkyl groups (assuming the designated length encompasses the particular example) are methyl, ethyl, propyl, isopropyl, butyl, sec-butyl, tertiary butyl, pentyl, isopentyl, hexyl and isohexyl.

By alkoxy is meant straight chain or branched saturated alkyl bonded through an oxy. Exemplary of such alkoxy groups (assuming the designated length encompasses the particular example) are methoxy, ethoxy, propoxy, isopropoxy, butoxy, isobutoxy, tertiary butoxy, pentoxy, isopentoxy, hexoxy and isohexoxy.

The expression "pharmaceutically-acceptable anionic salt" refers to nontoxic anionic salts containing anions such as (but not limited to) chloride, bromide, iodide, sulfate, bisulfate, phosphate, acetate, maleate, fumarate, oxalate, lactate, tartrate, citrate, gluconate, methanesulfonate and 4-toluene-sulfonate.

The expression "pharmaceutically-acceptable cationic salt" refers to nontoxic cationic salts such as (but not limited to) sodium, potassium, calcium, magnesium, ammonium or protonated benzathine (N,N'-dibenzylethylenediamine), choline, ethanolamine, diethanolamine, ethylenediamine, meglamine (N-methyl-glucamine), benethamine (N-benzylphenethylamine), piperazine or tromethamine (2-amino-2-hydroxymethyl-1,3-propanediol).

The expression "prodrug" refers to compounds that are drug precursors, which following administration, release the drug in vivo via some chemical or physiological process (e.g., a prodrug on being brought to the physiological pH is converted to the desired drug form). Exemplary prodrugs upon cleavage release the corresponding free acid, and such hydrolyzable ester-forming residues of the compounds of Formula I and IA include but are not limited to carboxylic acid substituents (e.g., $R_{10}$ contains carboxy) wherein the free hydrogen is replaced by $(C_1-C_4)$alkyl, $(C_2-C_{12})$ alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as α-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Other exemplary prodrugs release an alcohol of Formula I of IA wherein the free hydrogen of the hydroxy substituent (e.g., $R_5$ is hydroxy) is replaced by $(C_1-C_6)$ alkanoyloxymethyl, 1-(($C_1-C_6$)alkanoyloxy)ethyl, 1-methyl-1-(($C_1-C_6$)alkanoyloxy)ethyl, $(C_1-C_6)$ alkoxycarbonyloxymethyl, N-$(C_1-C_6)$ alkoxycarbonylaminomethyl, succinoyl, $(C_1-C_6)$alkanoyl, α-amino$(C_1-C_4)$alkanoyl, arylactyl and α-aminoacyl, or α-aminoacyl-α-aminoacyl wherein said α-aminoacyl moieties are independently any of the naturally occurring L-amino acids found in proteins, $P(O)(OH)_2$, $-P(O)(O (C_1-C_6)alkyl)_2$ or glycosyl (the radical resulting from detachment of the hydroxyl of the hemiacetal of a carbohydrate).

Other exemplary prodrugs include but are not limited to derivatives of Formula I or IA wherein $R_2$ is a free hydrogen which is replaced by R-carbonyl, RO-carbonyl, NRR'-carbonyl where R and R' are each independently (($C_1-C_{10}$) alkyl, ($C_3-C_7$)cycloalkyl, benzyl, or R-carbonyl is a natural α-aminoacyl or natural α-aminoacyl-natural α-aminoacyl, —C(OH)C(O)OY wherein Y is H, ($C_1-C_6$)alkyl or benzyl, —C(OY$_0$)Y$_1$ wherein Y$_0$ is $(C_1-C_4)$ alkyl and Y$_1$ is (($C_1-C_6$)alkyl, carboxy($C_1-C_6$)alkyl, amino($C_1-C_4$)alkyl or mono-N- or di-N,N-($C_1-C_6$)alkylaminoalkyl, —C(Y$_2$)Y$_3$ wherein Y$_2$ is H or methyl and Y$_3$ is mono-N— or di-N,N-

($C_1$–$C_6$)alkylamino, morpholino, piperidin-1-yl or pyrrolidin-1-yl.

Other exemplary prodrugs include but are not limited to derivatives of Formula I or IA bearing a hydrolyzable moiety at $R_3$, which release a compound of formula I or IA wherein $R_3$ is a free hydrogen on hydrolysis. Such hydrolyzable moieties at $R_3$ are/include 1-hydroxy($C_1$–$C_6$)alkyl or 1-hydroxy-1-phenylmethyl.

Other exemplary prodrugs include cyclic structures such as compounds of Formula I or IA wherein $R_2$ and $R_3$ are a common carbon, thus forming a five-membered ring. The linking carbon may be mono- or di-substituted independently with H, ($C_1$–$C_6$)alkyl, ($C_3$–$C_6$)cycloalkyl or phenyl. Alternatively, $R_3$ and $R_5$ may be taken together to form an oxazolidine ring and the number 2 carbon of the oxazolidine ring may be mono- or di-substituted independently with H, ($C_1$–$C_6$)alkyl, ($C_3$–$C_6$)cycloalkyl or phenyl.

Mammals treated according to the invention include but are not limited to humans. In one embodiment, the mammal is a companion animal, such as a dog or cat.

The chemist of ordinary skill will recognize that certain compounds of Formula I and IA contain one or more atoms which may be in a particular stereochemical or geometric configuration, giving rise to stereoisomers and configurational isomers. Examples of such atoms are the carbon atoms labelled (a) and (b) in Formula I, and the carbon atom labelled (a) in Formula 1A. All such isomers and mixtures thereof are included in the method and composition of the invention. Hydrates of the compounds of Formula I and IA are also included.

The compounds of Formula I and IA have asymmetric carbon atoms and therefore are enantiomers or diastereomers. Diasteromeric mixtures can be separated into their individual diastereomers on the basis of their physical chemical differences by methods known per se., for example, by chromatography and/or fractional crystallization. Enantiomers can be separated by converting the enantiomeric mixture into a diasteromeric mixture by reaction with an appropriate optically active compound (e.g., alcohol), separating the diastereomers and converting (e.g., hydrolyzing) the individual diastereomers to the corresponding pure enantiomers. All such isomers, including diastereomers, enantiomers and mixtures thereof are considered as part of the method and composition of this invention. Use of any tautomers of compounds of Formula I and IA is also encompassed by the invention.

Although many compounds employed in this invention are not ionizable at physiological conditions, some of the compounds employed in this invention are ionizable at physiological conditions. Thus, for example some of the compounds employed in this invention are acidic and they form a salt with a pharmaceutically acceptable cation. All such salts are within the scope of the method and composition of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, some of the compounds employed in this invention are basic, and they form a salt with a pharmaceutically acceptable anion. All such salts are within the scope of the method and composition of this invention and they can be prepared by conventional methods. For example, they can be prepared simply by contacting the acidic and basic entities, usually in a stoichiometric ratio, in either an aqueous, non-aqueous or partially aqueous medium, as appropriate. The salts are recovered either by filtration, by precipitation with a non-solvent followed by filtration, by evaporation of the solvent, or, in the case of aqueous solutions, by lyophilization, as appropriate.

In addition, use of any hydrates or solvates of compounds of formula I or IA is also within the scope of the invention.

Glycogen phosphorylase inhibition is readily determined by those skilled in the art according to standard assays.

Methods for obtaining glycogen phosphorylases, and assays for determining glycogen phosphorylase inhibition are described below. Other sources of glycogen phosphorylase, and other glycogen phosphorylase inhibition assays, are known in the art. For example the glycogen phosphorylase of U.S. Pat. No. 5,882,885 may also be employed.

Purification, Expression, and Assaying of Glycogen Phosphorylase from Pathogens:

Methods and strategies for cloning and expressing glycogen phosphorylase from bacteria or other pathogens are known in the art of molecular biology. In general, primers are designed to encompass the desired glycogen phosphorylase. The specific PCR product containing the desired glycogen phosphorylase is amplified, purified, and inserted into an appropriate plasmid to allow expression of the heterologous protein in *E. coli* under the control of a regulated promoter (e.g., trp or lac). To simplify purification, a host cell is preferably employed that lacks phoA, an endogenous phosphatase that is known to interfere with the assaying of glycogen phosphorylase. Purification of the enzyme can be accomplished by the procedure of Seok, et. al. (Seok, et al., 1997, J. Biol. Chem. 272:26511–26521) or by using tags (e.g., his tags or protein fusions) that aid in purification. Assay of glycogen phosphorylases from different bacteria may require optimization of the reaction conditions following purification of the enzyme activity. The assay can be run in either a forward or reverse manner (the forward direction monitors production of glucose-i-phosphate from glycogen or another substrate; the reverse reaction measures production of glycogen from glucose-1-phosphate by monitoring the release of inorganic phosphate).

To assess the activity of a compound for general antibacterial activity, those skilled in the art can follow guidelines developed by the National Committee for Clinical Laboratory Standards (Methods for dilution antimicrobial susceptibility tests for bacteria that grow aerobically—$4^{th}$ Edition; Approved Standard. NCCLS document M7-A4 (ISBN 1-56238-309-4) 1997; Methods for antimicrobial susceptibility testing of anaerobic bacteria—$3^{rd}$ Edition; Approved Standards. NCCLS document M11-A3 (ISBN 1-56238-210-1) 1993). Assays for determining antibacterial activity against intracellular pathogens vary according to the proscribed literature for each organism. Some specific examples and details are described below. Tests for determining activity against other organisms are known in the art.

Methodology for Testing of *Mycobacterium avium:*

Both agar and broth dilution assays can be performed to determine the in vitro susceptibility (MIC) of *Mycobacterium avium* complex (Inderlied, C. B. et al., Antimicrob. Agents Chemother., 1987, 31:1697–1702.). For determining the susceptibility of *M. avium* while growing intracellularly in human monocytes, 100 µL of a well-dispersed suspension of *M. avium* cells (final concentration of ~$5\times10^7$ cells/mL)

is added to each well of a 24-well tissue culture plate containing monocytes (as described by Bermudez, L. E., et al., Antimicrob Agents Chemother., 1996, 40:546–551). After 4 hours, quantitative plate counts of lysed macrophage monolayers are performed to establish the baseline of $M.$ $avium$ cells/mL within the macrophages. Infected monclayers are then treated with compound at different concentrations; compound and medium are replenished daily for 4 days. After the 4-day treatment period, the medium is removed and the monolayers are lysed using ice-cold sterile water, followed by a lysing solution containing sodium dodecyl sulfate. The final macrophage lysate suspension is serially diluted and aliquots (0.1 mL) are plated in duplicate on Middlebrook 7H10 agar. Results can be reported as mean numbers of colony-forming units per milliliter of macrophage lysate, with each assay performed in triplicate. The MIC is the lowest concentration of drug that results in 99.9% killing.

Methodology for Testing of *Legionella pneumophila*

MICs are performed according to NCCLS guidelines in 96-well microtiter trays (National Committee for Clinical Laboratory Standards 1990). A human monocyte cell line HL-60 ($1.5 \times 10^6$ cells/well) is infected with $1.5 \times 10^7$ colony-forming units of *L. pneumophilia*; after 6 h, the extracellular bacteria are removed by 4 washes, and compound added at varying concentrations. After 48 h, cells are removed with trypsin-EDTA and cell-associated bacteria counted from duplicate wells by hypotonic lysis of the cells with sterile distilled water, followed by serial dilution and plate counts on buffered yeast extract agar containing 0.1% α-keto glutarate (Stout, J. E. et al., Diagnostic Microbiology and Infectious Disease, 1998, 30:37–43). The MIC is the lowest concentration of drug that results in 99.9% killing.

Methodology for Testing of *Toxoplasma gondii*

Human foreskin fibroblast (HFF) cells (ATCC HS68) are grown in Dulbecco's modified Eagle's medium (Gibco BRL, Grand Island, N.Y.) containing 100 U of penicillin, 1 μg of streptomycin per ml, and 10% heat-inactivated *T. gondii* antibody-negative fetal bovine serum. In vitro activity is defined as the capacity of a compound to inhibit intracellular replication of *T. gondii* and is determined by the [$^3$H]uracil incorporation technique (Khan, et al., Antimicrob. Agents Chemother, 1996, 40:1855–1859). Briefly, the protocol consists of plating HFF cells at $10^4$ cells/well in 96-well flat-bottom tissue culture microtiter plates, followed by incubation at 37° C. in a 5% $CO_2$ incubator. After confluence, the monolayers are infected with tachyzoites at a ratio of three tachyzoites/cell. Four hours later, the monolayers are washed, compounds are added at varying concentrations, and the cultures incubated for 48 h. Four hours prior to harvesting of the cells, [$^3$H]uracil (1 μCi/well) is added and its level of incorporation determined. The cells are collected with a cell harvester, and the radioactivity counted with a scintillation counter. Compounds are compared by their $IC_{50}$ values, i.e., the concentration that inhibits 50% of [$^3$H]uracil incorporation uptake and incorporation.

Methods for testing of activity against *Chlamydia pneumoniae* are described in the Examples below.

Glycogen Phosphorylase from Mammalian Sources:

The three different purified glycogen phosphorylase (GP) isoenzymes from a human source, wherein glycogen phosphorylase is in the activated "a" state (referred to as glycogen phosphorylase a, or the abbreviation GPa), and referred to here as human liver glycogen phosphorylase a (HLGPa), human muscle glycogen phosphorylase a (HMGPa), and human brain glycogen phosphorylase a (HBGPa), can be obtained by the following procedures.

Expression and Fermentation

The HLGP, and HMGP cDNAs are expressed from plasmid pKK233-2 (Pharmacia Biotech. Inc., Piscataway, N.J.) in *E. coli* strain XL-1 Blue (Stratagene Cloning Systems, Lajolla, Calif.). The strain is inoculated into LB medium (consisting of 10 g tryptone, 5 g yeast extract, 5 g NaCl, and 1 ml 1N NaOH per liter) plus 100 mg/L ampicillin, 100 mg/L pyridoxine and 600 mg/L $MnCl_2$ and grown at 37° C. to a cell density of $OD_{550}=1.0$. At this point, the cells are induced with 1 mM isopropyl-1-thio-β-D-galactoside (IPTG). Three hours after induction the cells are harvested by centrifugation and cell pellets are frozen at −70° C. until needed for purification.

The HBGP cDNA can be expressed by several methodologies, for example, by the method described by Crerar, et al. (J. Biol. Chem. 270:13748–13756). The method described by Crerar, et al. for the expression of HBGP is as follows: the HBGP cDNA can be expressed from plasmid pTACTAC in *E. Coli* strain 25A6. The strain is inoculated into LB medium (consisting of 10 g tryptone, 5 g yeast extract, 5 g NaCl, and 1 ml 1 N NaOH per liter) plus 50 mg/L ampicillin and grown overnight, then resuspended in fresh LB medium plus 50 mg/L ampicillin, and reinoculated into a 40x volume of LB/amp media containing 250 μM isopropyl-1-thio-β-D-galactoside (IPTG), 0.5 mM pyridoxine and 3 mM mg/L and grown at 22° C. for 48–50 hours. The cells can then be harvested by centrifugation and cell pellets are frozen at −70° C. until needed for purification.

The HLGP cDNA is expressed from plasmid pBlueBac III (Invitrogen Corp., San Diego, Calif.) which is cotransfected with BaculoGold Linear Viral DNA (Pharmingen, San Diego, Calif.) into Sf9 cells. Recombinant virus is subsequently plaque-purified. For production of protein, Sf9 cells grown in serum-free medium are infected at an moi of 0.5 and at a cell density of $2 \times 10^6$ cells/ml. After growth for 72 hours at 27° C., cells are centrifuged, and the cell pellets frozen at −70° C. until needed for purification.

Purification of Mammalian Glycogen Phosphorylase Expressed in *E. coli*

The *E. coli* cells in pellets described above are resuspended in 25 mM β-glycerophosphate (pH 7.0) with 0.2 mM DTT, 1 mM $MgCl_2$, plus the following protease inhibitors:

| | |
|---|---|
| 0.7 μg/mL | Pepstatin A |
| 0.5 μg/mL | Leupeptin |
| 0.2 mM | phenylmethylsulfonyl fluoride (PMSF), and |
| 0.5 mM | EDTA, | lysed by pretreatment with 200 μg/mL lysozyme and 3 pg/mL DNAase followed by sonication in 250 mL batches for 5×1.5 minutes on ice using a Branson Model 450 ultrasonic cell disrupter (Branson Sonic Power Co., Danbury Conn). The *E. coli* cell lysates are then cleared by centrifugation at 35,000×g for one hour followed by filtration through 0.45 micron filters GP in the soluble fraction of the lysates (estimated to be less than 1% of the total protein) is purified by monitoring the enzyme activity (as described in GPa Activity Assay section, below) from a series of chromatographic steps detailed below.

Immobilized Metal Affinity Chromatography (IMAC)

This step is based on the method of Luong et al. (Luong et al. Journal of Chromatography (1992) 584, 77–84). 500 mL of the filtered soluble fraction of cell lysates (prepared from approximately 160–250 g of original cell pellet) are loaded onto a 130 mL column of IMAC Chelating- Sepharose (Pharmacia LKB Biotechnology, Piscataway, N.J.) which has been charged with 50 mM $CuCl_2$ and 25 mM β-glycerophosphate, 250 mM NaCl and 1 mM imidazole at pH 7 equilibration buffer. The column is washed with equilibration buffer until the A280 returns to baseline. The sample is then eluted from the column with the same buffer containing 100 mM imidazole to remove the bound GP and other bound proteins. Fractions containing the GP activity are pooled (approximately 600 mL), and ethylenediaminetetraacetic acid (EDTA), DL-dithiothreitol (DTT), phenylmethylsulfonyl fluoride (PMSF), leupeptin and pepstatin A are added to obtain 0.3 mM, 0.2 mM, 0.2 mM, 0.5 μg/mL and 0.7 μg/mL concentrations respectively. The pooled GP is desalted over a Sephadex G-25 column (Sigma Chemical Co., St. Louis, Mo.) equilibrated with 25 mM Tris-HCl (pH 7.3), 3 mM DTT buffer (Buffer A) to remove imidazole and is stored on ice until the second chromatographic step.

5'- AMP-Sepharose Chromatography

The desalted pooled GP sample (approximately 600 mL) is next mixed with 70 mL of 5'-AMP Sepharose (Pharmacia LKB Biotechnology, Piscataway, N.J.) which has been equilibrated with Buffer A (see above). The mixture is gently agitated for one hour at 22° C. then packed into a column and washed with Buffer A until the $A_{280}$ returns to baseline. GP and other proteins are eluted from the column with 25 mM Tris-HCl, 0.2 mM DTT and 10 mM adenosine 5'-monophosphate (AMP) at pH 7.3 (Buffer B). GP-containing fractions are pooled following identification by determining enzyme (described below) activity and visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM β-glycerophosphate, 0.2 mM DTT, 0.3 mM EDTA, 200 mM NaCl, pH 7.0 buffer (Buffer C) and stored on ice until use.

Prior to use of the GP enzyme, the enzyme is converted from the inactive form as expressed in *E. coli* strain XL-1 Blue (designated GPb) (Stratagene Cloning Systems, La Jolla, Calif.), to the active form (designated GPa) by the procedure described in the section Activation of GP below.

Purification of Glycogen Phosphorylase Expressed in Sf9 Cells

The Sf9 cells in pellets described above are resuspended in 25 mM β-glycerophosphate (pH 7.0) with 0.2 mM DTT, 1 mM MgCl2, plus the following protease inhibitors:

| | |
|---|---|
| 0.7 μg/mL | Pepstatin A |
| 0.5 μg/mL | Leupeptin |
| 0.2 mM | phenylmethylsulfonyl fluoride (PMSF), and |
| 0.5 mM | EDTA, | lysed by pretreatment with 3 μg/mL DNAase followed by sonication in batches for 3×1 minutes on ice using a Branson Model 450 ultrasonic cell disrupter (Branson Sonic Power Co., Danbury Conn.). The Sf9 cell lysates are then cleared by centrifugation at 35,000×g for one hour followed by filtration through 0.45 micron filters. GP in the soluble fraction of the lysates (estimated to be 1.5% of the total protein) is purified by monitoring the enzyme activity (as described in GPa Activity Assay section, below) from a series of chromatographic steps detailed below.

Immobilized Metal Affinity Chromatography (IMAC)

Immobilized Metal Affinity Chromatography is performed as described in the section above. The pooled, desalted GP is then stored on ice until further processed.

Activation of GP

Before further chromatography, the fraction of inactive enzyme as expressed in Sf9 cells (designated GPb) is converted to the active form (designated GPa) by the following procedure described in Activation of GP below.

Anion Exchange Chromatography

Following activation of the IMAC purified GPb to GPa by reaction with the immobilized phosphorylase kinase, the pooled GPa fractions are dialyzed against 25 mM Tris-HCl, pH 7.5, containing 0.5 mM DTT, 0.2 mM EDTA, 1.0 mM phenylmethylsulfonyl fluoride (PMSF), 1.0 pg/mL leupeptin and 1.0 pg/mL pepstatin A. The sample is then loaded onto a MonoQ Anion Exchange Chromatography column (Pharmacia Biotech. Inc., Piscataway, N.J.). The column is washed with equilibration buffer until the $A_{280}$ returns to baseline. The sample is then eluted from the column with a linear gradient of 0–0.25 M NaCl to remove the bound GP and other bound proteins. GP-containing fractions elute between 0.1–0.2 M NaCl range, as detected by monitoring the eluant for peak protein absorbance at $A_{280}$. The GP protein is then identified by visualizing the $M_r$ approximately 97 kdal GP protein band by sodium dodecyl sulfate polyacrylamide gel electrophoresis (SDS-PAGE) followed by silver staining (2D-silver Stain II "Daiichi Kit", Daiichi Pure Chemicals Co., LTD., Tokyo, Japan) and then pooled. The pooled GP is dialyzed into 25 mM BES, 1.0 mM DTT, 0.5 mM EDTA, 5 mM NaCl, pH 6.8 buffer and stored on ice until use.

Determination of GP Enzyme Activity

Activation of GP: Conversion of GPb to GPa

Prior to the determination of GP enzyme activity, the enzyme is converted from the inactive form as expressed in *E. coli* strain XL-1 Blue (designated GPb) (Stratagene Cloning Systems, La Jolla, Calif.), to the active form (designated GPa) by phosphorylation of GP using phosphorylase kinase as follows. The fraction of inactive enzyme as expressed in Sf9 cells (designated GPb) is also converted to the active form (designated GPa) by the follow procedure.

GP reaction with Immobilized Phosphorylase Kinase

Phosphorylase kinase (Sigma Chemical Company, St. Louis, Mo.) is immobilized on Affi-Gel 10 (BioRad Corp., Melville, N.Y.) as per the manufacturer's instructions. In brief, the phosphorylase kinase enzyme (10 mg) is incubated with washed Affi-Gel beads (1 mL) in 2.5 mL of 100 mM HEPES and 80 mM $CaCl_2$ at pH 7.4 for 4 hours at 4° C. The Affi-Gel beads are then washed once with the same buffer prior to blocking with 50 mM HEPES and 1 M glycine methyl ester at pH 8.0 for one hour at room temperature. Blocking buffer is removed and replaced with 50 mM HEPES (pH 7.4), 1 mM β-mercaptoethanol and 0.2% $NaN_3$ for storage. Prior to use to convert GPb to GPa, the Affi-Gel immobilized phosphorylase kinase beads are equilibrated by washing in the buffer used to perform the kinase reaction, consisting of 25 mM β-glycerophosphate, 0.3 mM DTT, and 0 3mM EDTA at pH 7.8 (kinase assay buffer).

The partially purified, inactive GPb obtained from 5'-AMP-Sepharose chromatography above (from *E. coli*) or the mixture of GPa and GPb obtained from IMAC above (from Sf9 cells) is diluted 1:10 with the kinase assay buffer then mixed with the aforementioned phosphorylase kinase enzyme immobilized on the Affi-Gel beads. NaATP is added to 5 mM and $MgCl_2$ to 6 mM. The resulting mixture is mixed gently at 25° C. for 30 to 60 minutes. The sample is removed from the beads and the percent activation of GPb by conversion to GPa is estimated by determining GP enzyme activity in the presence and absence of 3.3 mM AMP. The percent of total GP enzyme activity due to GPa enzyme activity (AMP-independent) is then calculated as follows:

((HLGP activity−AMP)/(HLGP activity+AMP)) 100

Alternately, the conversion of GPb to GPa can be monitored by isoelectric focusing based on the shift in electrophoretic mobility that is noted following conversion of GPb to GPa GP samples are analyzed by isoelectric focusing (IEF) utilizing the Pharmacia PfastGel System (Pharmacia Biotech. Inc., Piscataway, N.J.) using precast gels (pl range 4–6.5) and the manufacturer's recommended method. The resolved GPa and GPb bands are then visualized on the gels by silver staining (2D-silver Stain II "Daiichi Kit", Daiichi Pure Chemicals Co., LTD., Tokyo, Japan). Identification of GPa and GPb is made by comparison to E. coli derived GPa and GPb standards that are run in parallel on the same gels as the experimental samples.

GPa Activity Assay

The effect of the compounds of Formula I or IA on the activity of the activated form of glycogen phosphorylase (GPa) can be determined by one of two methods; glycogen phosphorylase a activity is measured in the forward direction by monitoring the production of glucose-1-phosphate from glycogen or by following the reverse reaction, measuring glycogen synthesis from glucose-1-phosphate by the release of inorganic phosphate. All reactions are run in triplicate in 96-well microtiter plates and the change in absorbance due to formation of the reaction product is measured at the wavelength specified below in a MCC/340 MKII Elisa Reader (Lab Systems, Finland), connected to a Titertech Microplate Stacker (ICN Biomedical Co, Huntsville, Ala.).

To measure the GPa enzyme activity in the forward direction, the production of glucose-1-phosphate from glycogen is monitored by the multienzyme coupled general method of Pesce et al. (Pesce, M. A., Bodourian, S. H., Harris, R. C. and Nicholson, J. F. (1977) Clinical Chemistry 23, 1711–1717) modified as follows: 1 to 100 pg GPa, 10 units phosphoglucomutase and 15 units glucose-6-phosphate dehydrogenase (Boehringer Mannheim Biochemicals, Indianapolis, Ind.) are diluted to 1 mL in Buffer A (described hereinafter). Buffer A is at pH 7.2 and contains 50 mM HEPES, 100 mM KCl, 2.5 mM ethyleneglycoltetraacetic acid (EGTA), 2.5 mM $MgCl_2$, 3.5 mM $KH_2PO_4$ and 0.5 mM dithiothreitol. 20 μl of this stock is added to 80 μl of Buffer A containing 0.47 mg/mL glycogen, 9.4 mM glucose, 0.63 mM of the oxidized form of nicotinamide adenine dinucleotide phosphate (NADP+). The compounds to be tested are added as 5 μL of solution in 14% dimethylsulfoxide (DMSO) prior to the addition of the enzymes. The basal rate of GPa enzyme activity in the absence of inhibitors is determined by adding 5 μL of 14% DMSO and a fully-inhibited rate of GPa enzyme activity is obtained by adding 20 μL of 50 mM of the positive control test substance, caffeine. The reaction is followed at room temperature by measuring the conversion of oxidized NADP+ to reduced NADPH at 340 nm.

To measure the GPa enzyme activity in the reverse direction, the conversion of glucose-1-phosphate into glycogen plus inorganic phosphate is measured by the general method described by Engers et al. (Engers, H. D., Shechosky, S. and Madsen, N. B. (1970) Can. J Biochem. 48, 746–754) modified as follows: 1 to 100 ug GPa is diluted to 1 mL in Buffer B (described hereinafter). Buffer B is at pH 7.2 and contains 50 mM HEPES, 100 mM KCl, 2.5 mM EGTA, 2 5 mM $MgCl_2$ and 0.5 mM dithiothreitol. 20 μL of this stock is added to 80 μL of Buffer B with 1.25 mg/mL glycogen, 9.4 mM glucose, and 0.63 mM glucose-1-phosphate. The compounds to be tested are added as 5 μL of solution in 14% DMSO prior to the addition of the enzyme. The basal rate of GPa enzyme activity in the absence of added inhibitors is determined by adding 5 μL of 14% DMSO and a fully-inhibited rate of GPa enzyme activity is obtained by adding 20 μL of 50 mM caffeine. This mixture is incubated at room temperature for 1 hour and the inorganic phosphate released from the glucose-1-phosphate is measured by the general method of Lanzetta et al. (Lanzetta, P. A., Alvarez, L. J., Reinach, P. S. and Candia, O. A. (1979) Anal. Biochem. 100, 95–97) modified as follows: 150 μL of 10 mg/mL ammonium molybdate, 0.38 mg/mL malachite green in 1 N HCl is added to 100 μL of the enzyme mix. After a 20 minute incubation at room temperature, the absorbance is measured at 620 nm.

The above assays can also be used to assess activity of glycogen phosphorylase derived from various pathogenic sources. Adaptation of the assays as required is easily accomplished.

The above assays carried out with a range of concentrations of test compound allows the determination of an $IC_{50}$ value (concentration of test compound required for 50% inhibition) for the in vitro inhibition of GPa enzyme activity by that test compound.

The inhibiting effect of compounds employed in the invention on the human liver and human muscle glycogen phosphorylase a isoforms is shown in Table 1 below.

TABLE 1*

| Compound Name | HLGPa $IC_{50}$ nM | HMGPa $IC_{50}$ nM |
| --- | --- | --- |
| 5-chloro-1H-indole-2-carboxylic acid [(1S)-benzyl-(2R)-hydroxy-3-((3S)-hydroxy-pyrrolidin-1-yl)-3-oxopropyl]-amide | 54 | 96 |
| 5-chloro-1H-indole-2-carboxylic acid [(1S)-benzyl(2R)-hydroxy-3-((3S,4S)-dihydroxy-pyrrolidin-1-yl)-3-oxopropyl]-amide | 73 | 90 |
| 5-chloro-1H-indole-2-carboxylic acid [(1S)-benzyl-3-((3-hydroxy azetidin-1-yl)-(2R)-hydroxy-3-oxopropyl]-amide | 236 | 706 |
| 5-chloro-1H-indole-2-carboxylic acid [(1S)-benzyl-3-(cis-3,4-dihydroxy-pyrrolidin-1-yl)-(2R)-hydroxy-3-oxopropyl]-amide | 59 | 385 |
| 5-chloro-1H-indole-2-carboxylic acid [1-benzyl-2-(3-hydroxypyrrolidin-1-yl)-2-oxo-ethyl]-amide | 45 | 85 |
| 5-chloro-1H-indole-2-carboxylic acid [(1S)-benzyl-2-(cis-3,4-dihydroxypyrrolidin-1-yl)-2-oxo-ethyl]-amide | 30 | 97 |
| 5-chloro-1H-indole-2-carboxylic acid [(1S)-(4-fluorobenzyl-2-(4-hydroxy-piperidin-1-yl)-2-oxo-ethyl]-amide | 142 | 83 |
| 5-chloro-1H-indole-2-carboxylic acid (2-oxo-2-thiazolidin-3-yl-ethyl)-amide | 307 | 433 |

TABLE 1*-continued

| Compound Name | HLGPa IC$_{50}$ nM | HMGPa IC$_{50}$ nM |
|---|---|---|
| 5-chloro-1H-indole-2-carboxylic acid [(1S)-benzyl-2-(3-hydroxy-azetidin-1-yl)-2-oxo-ethyl]-amide | 65 | 121 |
| 5-chloro-1H-indole-2-carboxylic acid [(1S)-benzyl-2-(3-hydroxyimino-azetidin-1-yl)-2-oxo-ethyl]-amide | 65 | 84 |
| 5-chloro-1H-indole-2-carboxylic acid [(1S)-benzyl-2-((3S,4S)-dihydroxy-pyrrolidin-1-yl)-2-oxo-ethyl]-amide | 137 | 71 |

*data are for HLGPa and HMGPa enzyme activity (IC$_{50}$) as determined by the reverse direction assay.

Generally, the glycogen phosphorylase inhibitors are administered orally, but parenteral administration (e.g., intravenous, intramuscular, subcutaneous or intramedullary) may be utilized, for example, where oral administration is inappropriate or where the patient is unable to ingest the drug. For certain tissues such as the eye, topical administration may also be suitable.

The glycogen phosphorylase inhibitors may be administered alone or in combination with pharmaceutically acceptable carriers, in either single or multiple doses. Suitable pharmaceutical carriers include inert solid diluents or fillers, sterile aqueous solutions, oils (e.g., peanut oil, sesame oil) and various organic solvents. The pharmaceutical compositions formed by combining the active compounds and pharmaceutically acceptable carriers can then be readily administered in a variety of dosage forms such as tablets, powders, lozenges, emulsions, oil soft gels, syrups, injectable solutions, spray-dried formulations, transdermal or transmucosal patches, inhalable formulations and the like. These pharmaceutical compositions can, if desired, contain additional ingredients such as flavorings, binders, excipients and the like. Thus, for purposes of oral administration, tablets containing various excipients such as sodium citrate, calcium carbonate and calcium phosphate may be employed along with various disintegrants such as starch, methylcellulose, alginic acid and certain complex silicates, together with binding agents such as polyvinylpyrrolidone, sucrose, gelatin and acacia. Additionally, lubricating agents such as magnesium stearate, sodium lauryl sulfate and talc are often useful for tabletting purposes. Solid compositions of a similar type may also be employed as fillers in soft and hard filled gelatin capsules. Preferred materials for this include lactose or milk sugar and high molecular weight polyethylene glycols. When aqueous suspensions or elixirs are desired for oral administration, the essential active ingredient therein may be combined with various sweetening or flavoring agents, coloring matter or dyes and, if desired, emulsifying or suspending agents, together with diluents such as water, ethanol, propylene glycol, glycerin and combinations thereof.

For parenteral administration, solutions containing an active compound or a pharmaceutically acceptable salt thereof in sesame or peanut oil, aqueous propylene glycol, or in sterile aqueous solution may be employed. Such aqueous solutions should be suitably buffered if necessary and the liquid diluent first rendered isotonic with sufficient saline or glucose. These particular aqueous solutions are especially suitable for intravenous, intramuscular, subcutaneous and intraperitoneal administration. The sterile aqueous media employed are all readily available by standard techniques known to those skilled in the art.

Methods of preparing various pharmaceutical compositions with a certain amount of active ingredient are known, or will be apparent in light of this disclosure, to those skilled in this art. For examples of how to prepare such compositions see Remington's Pharmaceutical Sciences, Mack Publishing Company, Easton, Pa., 19th Edition (1995).

Pharmaceutical compositions administered according to the invention generally contain 0.01%–95% of glycogen phosphorylase inhibitor, preferably 1%–70%. In any event, the composition or formulation to be administered contains a quantity of a glycogen phosphorylase inhibitor in an amount effective to treat infection. Typically, an effective dosage for the glycogen phosphorylase inhibitor is in the range of about 0.005 to 50 mg/kg/day, preferably 0.01 to 25 mg/kg/day and most preferably 0.1 to 15 mg/kg/day.

The present invention encompasses treating or preventing infection by administering a compound of formula I in combination with a second compound for treating the infection. The second compound for treating the infection can be, for example, an antibiotic such as an aminoglycoside, penicillin, beta-lactamase inhibitor, anti-tuberculosis agent, cephalosporin, carbapenem, quinolone, macrolide, ketolide, oxazolidinone (i.e., linezolid), streptogramins, anti-staphylococcal agent, lincosamine, sulfonamide, or other type of antibiotic. Examples of such antibiotics include but are not limited to amoxicillin, ampicillin, polycillin, azithromycin, azlocillin, aztrenam, bacampicillin, bacitracin, benethamine, benza-thine, bicillin, benzylpenicillin, capreomycin, carbenicillin, cefadroxil, cefamandole, cefazolin, cefixime, cefizoxime, ceflacor, cefmetazole, cefoperazone, cefotaxime, cefotetan, cefoxitin, ceftazidime, ceftriaxone, cefuroxime, cephalexin, cephalothin, cephapirin, cephradine, chlorampenicol, chlortetracycline, cilastatin, ciprofloxacin, clarithromycin, clavulanic acid, clindamycin, colistin, cycloserine, dalfopristin, demeclocycline, dicloxacillin, doxycycline, erythrocin, erythromycin, ethambutol, ethionamide, fosfomycin, gentamicin, imipenem, isoniazid, kanamycin, lincomycin, linezolid, meropenem, methacycline, methenamine, mandelamine, methicillin, metronidazole, mezlocillin, minocycline, mupirocin, nafcillin, nalidixic acid, neomycin, netilmicin, nitrofurantoin, norfloxacin, novobiocin, ofloxacin, oxacillin, oxolinic acid, oxytetracycline, quinipristin, paromomycin, pefloxacin, phenoxymethylpenicillin, piperacillin, polymyxin b, procaine penicillin, pyrazinamide, r-aminosalicyclic acid, rifampin, spectinomycin, streptomycin, sulfacytine, sulfisoxazole, sullbacatam, Synercid, telithromycin, sulfadiazine, sulfamethizole, sulfamethoxazole, sulfapyridine, sulfasalazine, sulfisoxazole, sullbacatam, tetracycline, thienamycin, ticarcillin, ticarcillin, tobramycin, trimethoprim, trisulfapyrimidines, trovafloxicin, and vancomycin. Administration of these compounds can be carried out using dosages and formulations that are well-known.

The invention is illustrated by the following Example, which is provided to exemplify the invention, and not to be interpreted as narrowing its scope.

EXAMPLE

TABLE 2

Use of GP Inhibitors to treat *Chlamydia pneumoniae* infection

| | Protocol 1 | | Protocol 2 |
|---|---|---|---|
| Compound | MIC (μg/ml) | MBC (μg/ml) | MIC (μg/ml) |
| 1 | 12.5 | 25 | 12.5 |
| 2 | 25 | 25 | 50 |

Compounds used in this Example are shown below:

1

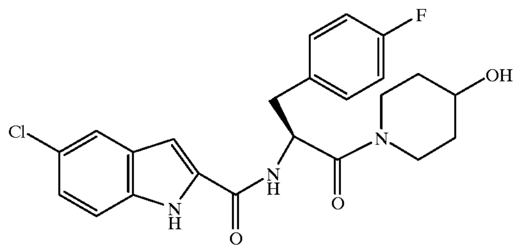

2

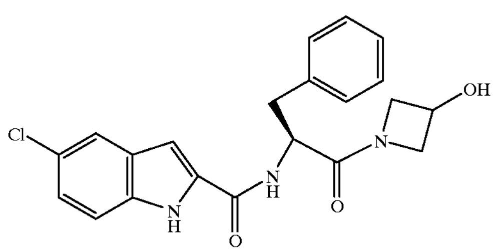

Protocol 1 was performed in 96-well flat-bottom microtiter plates. Each well contained 100 μL of $10^6$ HEp-G2 cells/ml in standard medium that had been incubated for 24 h at 37° C. in 5% $CO_2$. Compound stocks were prepared in dimethylsulfoxide, diluted in two-fold serial dilutions, and added to each well as 10 μL aliquots. Each compound concentration was assayed in triplicate. Elementary bodies (chlamydial stock) were diluted to contain $2\times10^4$inclusion-forming units (ifu) per milliliter and 90 μL was added to each well. Infection was allowed to proceed for 72 h at 37° C. in 5% $CO_2$, after which the cells were fixed and stained with genus-reactive anti-LPS antibody. The use of a fluorescein (FITC)-conjugated secondary antibody allowed the number of inclusion-containing cells to be identified via inverted fluorescent microscopy. The minimum inhibitory concentration (MIC) was defined as the lowest concentration of compound that inhibited the formation of inclusions. The minimal bactericidal concentration (MBC) was defined as the lowest concentration of compound that prevented the formation of inclusions after the compound had been removed by the addition of fresh medium and the cultures had been incubated for a further 48 h. Procedures for growth and preparation of C. pneumoniae and HEp-G2 cells are described in Kalayoglu, M. V., et al., J. Infect. Dis., 1999, 180:780–790. Methodology for detecting inclusions using an direct fluorescent antibody technique is found in Byrne, G. I., et al. J. Infect. Dis., 1993, 168:415–420.

Protocol 2 was nearly identical to protocol 1 except that compound was added 15 h after challenge of HEp-G2 cells with *C. pneumoniae*. This protocol helps distinguish compounds that interfere with latter stages of *C. pneumoniae* growth and replication.

As shown in Table 2, both compound I and compound 2 exhibited activity against growth of *C. pneumoniae* in HEp-2 cells. Compound 1 was superior to compound 2 in interfering with the latter stage of pneumoniae growth and replication. Also of note was that the MICs of compound I and compound 2 did not differ in a protocol that treats HEp-G2 cells with cycloheximide (1 μg/mL).

What is claimed is:

1. A method of treating a *Chiamydia pneumoniae* or a *Chlamydia trachomatis* infection in a mammal comprising administering an effective amount of a glycogen phosphorylase inhibitor of Formula I or Formula IA Formula I 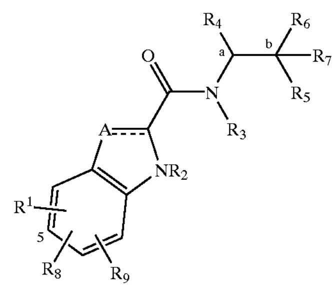 Formula IA 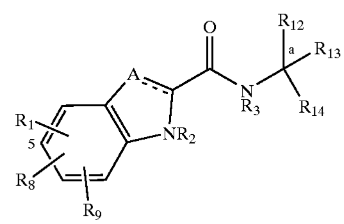 and the pharmaceutically acceptable salts and prodrugs thereof;

wherein:

the dotted line (---) is an optional bond;

A is —C(H)═, —C(($C_1$–$C_4$)alkyl)═ or —C(halo)═ when the dotted line (---) is a bond, or A is methylene or —CH(($C_1$–$C_4$)alkyl)- when the dotted line (---) is not a bond;

$R_1$, $R_8$ or $R_9$ are each independently H, halo, 4-, 6- or 7-nitro, cyano, ($C_1$–$C_4$)alkyl, ($C_1$–$C_4$)alkoxy, fluoromethyl, difluoromethyl or trifluoromethyl;

$R_2$ is H;

$R_3$ is H or ($C_1$–$C_5$)alkyl;

$R_4$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, phenyl($C_1$–$C_4$)alkoxy ($C_1$–$C_4$)alkyl, thien-2- or -3-yl($C_1$–$C_4$)alkyl or fur-2- or - 3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino or cyano; or $R_4$ is pyrid-2-, -3- or -4-yl($C_1$–$C_4$)alkyl, thiazol-2-, -4- or -5-yl($C_1$–$C_4$)alkyl, imidazol -1-, -2-, -4- or - 5-yl ($C_1$–$C_4$)alkyl, pyrrol-2- or -3-yl($C_1$–$C_4$)alkyl, oxazol-2-, - 4- or -5-yl-($C_1$–$C_4$)alkyl, pyrazol-3-, -4- or -5-yl($C_1$–$C_4$)alkyl, isoxazol-3-, -4- or -5-yl($C_1$–$C_4$)alkyl, isothiazol-3-, -4- or -5-yl($C_1$–$C_4$)alkyl, pyridazin-3- or -4-yl-($C_1$–$C_4$)alkyl, pyrimidin-2-, -4-, -5- or -6- yl($C_1$–$C_4$)alkyl, pyrazin-2- or -3-yl($C_1$–$C_4$)alkyl or 1,3, 5-triazin-2-yl($C_1$–$C_4$)alkyl, wherein said preceding $R_4$ heterocycles are optionally mono- or di-substituted independently with halo, trifluoromethyl, ($C_1$–$C_4$) alkyl, ($C_1$–$C_4$)alkoxy, amino or hydroxy and said mono-or di- substituents are bonded to carbon;

$R_5$ is H, hydroxy, fluoro, ($C_1$–$C_5$)alkyl, ($C_1$–$C_5$)alkoxy, ($C_1$–$C_6$)alkanoyl, amino($C_1$–$C_4$)alkoxy, mono-N- or di-N,N- ($C_1$–$C_4$)alkylamino($C_1$–$C_4$)alkoxy, carboxy ($C_1$–$C_4$)alkoxy, ($C_1$–$C_5$)alkoxy-carbonyl($C_1$–$C_4$) alkoxy, benzyloxycarbonyl($C_1$–$C_4$)alkoxy, or carbonyloxy wherein said carbonyloxy is carbon-carbon linked with phenyl, thiazolyl, imidazolyl, 1H-indolyl, furyl, pyrrolyl, oxazolyl, pyrazolyl, isoxazolyl, isothiazolyl, pyridazinyl, pyrimidinyl, pyrazinyl or 1,3,5-triazinyl and wherein said preceding $R_5$ rings are optionally mono-substituted with halo, ($C_1$–$C_4$)alkyl, ($C_1$–$C_4$) alkoxy, hydroxy, amino or trifluoromethyl and said mono-substituents are bonded to carbon;

$R_7$ is H, fluoro or ($C_1$–$C_5$)alkyl; or $R_5$ and $R_7$ can be taken together to be oxo;

$R_6$ is C(O)$R_{10}$;

$R_{10}$ is piperazin-1-yl, 4- ($C_1$–$C_4$)alkylpiperazin-1-yl, 4-formylpiperazin-1-yl, morpholino, thiomorpholino, 1-oxothiomorpholino, 1,1-dioxo-thiomorpholino, thiazolidin-3-yl, 1-oxo-thiazolidin-3-yl, 1,1-dioxo-thiazolidin-3-yl, 2-($C_1$–$C_6$)alkoxycarbonylpyrrolidin-1-yl, oxazolidin-3-yl or 2(R)-hydroxymethylpyrrolidin-1-yl; or $R_{10}$ is 3- and/or 4-mono-or di-substituted oxazetidin-2-yl, 2-, 4-, and/or 5- mono- or di-substituted oxazolidin-3-yl, 2-, 4-, and/or 5- mono- or di-substituted thiazolidin-3-yl, 2-, 4-, and/or 5- mono-or di- substituted 1-oxothiazolidin-3-yl, 2-, 4-, and/or 5- mono- or di-substituted 1,1-dioxothiazolidin-3-yl, 3- and/or 4-, mono- or di-substituted pyrrolidin-1-yl, 3-, 4- and/or 5-, mono-, di- or tri-substituted piperidin-1-yl, 3-, 4-, and/or 5- mono-, di-, or tri-substituted piperazin-1-yl, 3-substituted azetidin-1-yl, 4- and/or 5-, mono- or di-substituted 1,2-oxazinan-2-yl, 3-and/or 4-mono- or di-substituted pyrazolidin-1-yl, 4- and/or 5-, mono- or di-substituted isoxazolidin-2-yl, 4- and/or 5-, mono- and/or di-substituted isothiazolidin-2-yl wherein said $R_{10}$ substituents are independently H, halo, ($C_1$–$C_5$)-alkyl, hydroxy, amino, mono-N- or di-N,N- ($C_1$–$C_5$) alkylamino, formyl, oxo, hydroxyimino, ($C_1$–$C_5$) alkoxy, carboxy, carbamoyl, mono-N-or di-N,N- ($C_1$–$C_4$)alkylcarbamoyl, ($C_1$–$C_4$)alkoxyimino, ($C_1$–$C_4$)alkoxymethoxy, ($C_1$–$C_6$)alkoxycarbonyl, carboxy ($C_1$–$C_5$)alkyl or hydroxy($C_1$–$C_5$)alkyl;

$R_{12}$ is H, methyl, ethyl, n-propyl, hydroxy($C_1$–$C_3$)alkyl, ($C_1$–$C_3$)alkoxy($C_1$–$C_3$)alkyl, phenyl($C_1$–$C_4$)alkyl, phenylhydroxy($C_1$–$C_4$)alkyl, (phenyl) (($C_1$–$C_4$)-alkoxy) ($C_1$–$C_4$)alkyl, thien-2- or -3-yl($C_1$–$C_4$)alkyl or fur-2- or -3-yl($C_1$–$C_4$)alkyl wherein said $R_4$ rings are mono-, di- or tri-substituted independently on carbon with H, halo, ($C_1$–$C_4$)alkyl, ($C_1$–$C_4$)alkoxy, trifluoromethyl, hydroxy, amino, cyano or 4,5-dihydro-1H-imidazol-2-yl;

or $R_{12}$ is pyrid-2-, -3- or -4-yl($C_1$–$C_4$)alkyl, thiazol-2-, -4- or -5-yl($C_1$–$C_4$)alkyl, imidazol-2-, -4- or -5-yl($C_1$–$C_4$) alkyl, pyrrol-2- or -3-yl($C_1$–$C_4$)alkyl, oxazol-2-, 4- or -5-yl($C_1$–$C_4$)alkyl, pyrazol-3-, -4- or -5-yl($C_1$–$C_4$) alkyl, isoxazol-3-, -4- or -5-yl($C_1$–$C_4$)alkyl, isothiazol-3-, -4- or -5-yl($C_1$–$C_4$)alkyl, pyridazin-3-or -4-yl ($C_1$–$C_4$)alkyl, pyrimidin-2-, -4-, -5- or -6-yl($C_1$–$C_4$) alkyl, pyrazin-2- or -3-yl($C_1$–$C_4$)alkyl, 1,3,5-triazin-2-yl($C_1$–$C_4$)alkyl or indol-2-($C_1$–$C_4$)alkyl, wherein said preceding $R_{12}$ heterocycles are optionally mono- or di-substituted independently with halo, trifluoromethyl, ($C_1$–$C_4$)alkyl, ($C_1$–$C_4$)alkoxy, amino, hydroxy or cyano and said substituents are bonded to carbon; or $R_{12}$ is $R_{11}$-carbonyloxymethyl, wherein said $R_{11}$ is phenyl, thiazolyl, imidazolyl, 1H-indolyl, furyl, pyrrolyl, oxazolyl, pyrazolyl, isoxazolyl, isothiazolyl, pyridyl, pyridazinyl, pyrimidinyl, pyrazinyl or 1,3,5-triazinyl and wherein said preceding $R_{11}$ rings are optionally mono- or di-substituted independently with halo, amino, hydroxy, ($C_1$–$C_4$)alkyl, ($C_1$–$C_4$)alkoxy or trifluoromethyl and said mono- or di-substituents are bonded to carbon;

$R_{13}$ is H;

$R_{14}$ C(O)$R_{15}$;

$R_{15}$ is morpholino, thiomorpholino, 1-oxothiomorpholino, 1, 1-dioxothiomorpholino, thiazolidin-3-yl, 1-oxothiazolidin-3-yl, 1,1-dioxothiazolidin-3-yl, pyrrolidin-1-yl, piperidin-1-yl, piperazin-1-yl, piperazin-4-yl, azetidin-1-yl, 1,2-oxazinan-2-yl, pyrazolidin-1-yl, isoxazolidin-2-yl, isothiazolidin-2-yl, 1,2-oxazetidin-2-yl, oxazolidin-3-yl, 3,4-dihydroisoquinolin-2-yl, 1,3-dihydroisoindol-2-yl, 3,4-dihydro-2H-quinol-1-yl, 2,3-dihydro-benzo[1,4]oxazin-4-yl, 2,3-dihydro-benzo[1,4]-thiazine-4-yl, 3,4-dihydro-2H-quinoxalin-1-yl, 3,4-dihydro-benzo[c][1,2]oxazin-1-yl, 1,4-dihydro-benzo[d][1,2]oxazin-3-yl, 3,4-dihydro-benzo[e][1,2]-oxazin- 2-yl, 3H-benzo[d]isoxazol-2-yl, 3H-benzo[c]isoxazol-1-yl or azepan-1-yl, wherein said $R_{15}$ rings are optionally mono-, di- or tri-substituted independently with halo, ($C_1$–$C_5$) alkyl, ($C_1$–$C_5$)alkoxy, hydroxy, amino, mono-N- or di-N,N-($C_1$–$C_5$)alkylamino, formyl, carboxy, carbamoyl, mono-N- or di-N,N- ($C_1$–$C_5$) alkylcarbamoyl, ($C_1$–$C_6$)alkoxy($C_1$–$C_3$)alkoxy, ($C_1$–$C_5$)alkoxycarbonyl, benzyloxycarbonyl, ($C_1$–$C_5$) alkoxycarbonyl ($C_1$–$C_5$)alkyl, ($C_1$–$C_4$) alkoxycarbonylamino, carboxy($C_1$–$C_5$)alkyl, carbamoyl($C_1$–$C_5$)alkyl, mono-N- or di-N,N-($C_1$–$C_5$) alkylcarbamoyl($C_1$–$C_5$)alkyl, hydroxy($C_1$–$C_5$)alkyl, ($C_1$–$C_4$)alkoxy($C_1$–$C_4$)alkyl, amino($C_1$–$C_4$)alkyl, mono-N- or di-N,N- ($C_1$–$C_4$)alkylamino($C_1$–$C_4$)alkyl, oxo, hydroxyimino or ($C_1$–$C_6$)alkoxyimino and wherein no more than two substituents are selected from oxo, hydroxyimino or ($C_1$–$C_6$)alkoxyimino and oxo, hydroxyimino or ($C_1$–$C_6$)alkoxyimino are on non-aromatic carbon; and wherein said $R_{15}$ rings are optionally additionally mono- or di-substituted independently with ($C_1$–$C_5$)alkyl or halo.

2. A method according to claim 1 wherein:

$R_1$ is 5-H, 5-halo, 5-methyl or 5-cyano;

$R_8$ and $R_9$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di- substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol -1-, -2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is hydroxy; and $R_7$ is H.

3. A method according to claim 2 wherein:

the carbon atom labelled a has (S) stereochemistry;

the carbon atom labelled b has (R) stereochemistry;

$R_4$ is phenyl($C_1$–$C_2$)alkyl, thien-2-yl-($C_1$–$C_2$)alkyl, thien-3-yl-($C_1$–$C_2$)alkyl, fur-2-yl-($C_1$–$C_2$)alkyl or fur-3-yl-($C_1$–$C_2$)alkyl wherein said rings are mono- or di-substituted independently with H or fluoro; and $R_{10}$ is morpholino, 4-($C_1$–$C_4$)alkylpiperazin-1-yl, 3-substituted azetidin-1-yl, 3- and/or 4-, mono- or di-substituted pyrrolidin-1-yl, 4- and/or 5- mono- or di-substituted isoxazolidin-2-yl, 4- and/or 5-, mono- or di-substituted 1,2-oxazinan-2-yl wherein said substituents are each independently H, halo, hydroxy, amino, mono-N- or di-N,N-($C_1$–$C_6$)alkylamino, oxo, hydroxyimino or alkoxy.

4. A method according to claim 1 wherein the compound is of Formula I and wherein:

$R_1$ is H, halo, methyl or cyano;

$R_8$ and $R_9$ are each independently H or halo;

A is —C(H)=;

$R_2$ and $R_3$ are H;

$R_4$ is phenyl($C_1$–$C_2$)alkyl wherein said phenyl groups are mono-, di- or tri-substituted independently with H or halo or mono- or di- substituted independently with H, halo, ($C_1$–$C_4$)alkyl, ($C_1$–$C_4$)alkoxy, trifluoromethyl, hydroxy, amino or cyano; or $R_4$ is thien-2- or -3-yl($C_1$–$C_2$)alkyl, pyrid-2-, -3- or -4-yl ($C_1$–$C_2$)alkyl, thiazol-2-, -4- or -5-yl($C_1$–$C_2$)alkyl, imidazol -1-, -2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, -4- or -5-yl-($C_1$–$C_2$)alkyl, pyrazol-3-, -4- or -5-yl ($C_1$–$C_2$)alkyl, isoxazol-3-, -4- or -5-yl($C_1$–$C_2$)alkyl wherein said preceding $R_4$ heterocycles are optionally mono- or di-substituted independently with halo, trifluoromethyl, ($C_1$–$C_4$)alkyl, ($C_1$–$C_4$)alkoxy, amino or hydroxy and said mono- or di-substituents are bonded to carbon;

$R_5$ is fluoro, ($C_1$–$C_4$)alkyl, ($C_1$–$C_5$)alkoxy, amino($C_1$–$C_4$) alkoxy, mono-N- or di-N,N-($C_1$–$C_4$)alkylamino ($C_1$–$C_4$)alkoxy, carboxy($C_1$–$C_4$)alkoxy, ($C_1$–$C_5$) alkoxy-carbonyl($C_1$–$C_4$)alkoxy, benzyloxycarbonyl ($C_1$–$C_4$)alkoxy; and $R_7$ is H, fluoro or ($C_1$–$C_6$)alkyl.

5. A method according to claim 1 wherein said compound is selected from the group consisting of:

5-Chloro-1H-indole-2-carboxylic acid [(1S)-benzyl-(2R)-hydroxy-3-(4-methylpiperazin-1-yl)-3-oxo-propyl]-amide hydrochloride, 5-Chloro-1H-indole-2-carboxylic acid [(1S)-benzyl-(2R)-hydroxy-3-(3-hydroxyazetidin-1-yl)-3-oxo-propyl]-amide, 5-Chloro-1H-indole-2-carboxylic acid ((1S)-benzyl-(2R)-hydroxy-3-isoxazolidin-2-yl-3-oxo-propyl)-amide, 5-Chloro-1H-indole-2-carboxylic acid ((1S)-benzyl-(2R)-hydroxy-3-[1,2]oxazinan-2-yl-3-oxo-propyl)-amide, 5-Chloro-1H-indole-2-carboxylic acid [(1S)-benzyl-(2R)-hydroxy-3-((3S)-hydroxypyrrolidin-1-yl)-3-oxo-propyl]-amide, 5-Chloro-1H-indole-2-carboxylic acid [(1S)-benzyl-3-((3S,4S)-dihydroxy-pyrrolidin-1-yl)-(2R)-hydroxy-3-oxo-propyl]-amide, 5-Chloro-1H-indole-2-carboxylic acid [(1S)-benzyl-3-(cis-3,4-dihydroxy-pyrrolidin-1-yl)-(2R)-hydroxy-3-oxo-propyl]-amide; and 5-Chloro-1H-indole-2-carboxylic acid ((1S)-benzyl-(2R)-hydroxy-3-morpholin-4-yl-3-oxo-propyl)-amide.

6. A method according to claim 1 wherein the compound is of the Formula IA, and wherein:

$R_1$ is 5-H, 5-halo, 5-methyl, 5-cyano or 5-trifluoromethyl;

$R_8$ and $R_9$ are each independently H or halo;

A is —C(H)=;

$R_2$ and $R_3$ are H; and $R_{12}$ is H, methyl, phenyl($C_1$–$C_2$)alkyl, wherein said phenyl groups are mono- or di-substituted independently with H, halo, ($C_1$–$C_4$)alkyl, ($C_1$–$C_4$)alkoxy, trifluoromethyl, hydroxy, amino or cyano and wherein said $R_{12}$ groups are optionally additionally monosubstituted with halo; or $R_{12}$ is thien-2- or -3-yl($C_1$–$C_2$)alkyl, pyrid-2-, -3- or -4-yl($C_1$–$C_2$)alkyl, thiazol-2-, -4- or -5-yl($C_1$–$C_2$)alkyl, imidazol-2-, -4- or -5-yl($C_1$–$C_2$)alkyl, fur-2- or -3-yl ($C_1$–$C_2$)alkyl, pyrrol-2- or -3-yl($C_1$–$C_2$)alkyl, oxazol-2-, - 4- or -5-yl($C_1$–$C_2$)alkyl, pyrazol-3-, -4- or -5-yl ($C_1$–$C_2$)alkyl, isoxazol-3-, -4- or -5-yl($C_1$–$C_2$)alkyl, isothiazol-3-, -4- or -5-yl($C_1$–$C_2$)alkyl, pyridazin-3- or -4-yl($C_1$–$C_2$)alkyl, pyrimidin-2-, -4-, -5- or -6-yl ($C_1$–$C_2$)alkyl, pyrazin-2- or -3-yl($C_1$–$C_2$)alkyl or 1,3,5-triazin-2-yl($C_1$–$C_2$)alkyl wherein said preceding $R_{12}$ heterocycles are optionally mono- or di-substituted independently with halo, trifluoromethyl, ($C_1$–$C_4$) alkyl, ($C_1$–$C_4$)alkoxy, amino or hydroxy and said mono- or di- substituents are bonded to carbon.

7. A method according to claim 1 wherein said compound is selected from the group consisting of:

5-Chloro-1H-indole-2-carboxylic acid [(1S)-benzyl-2-(3-hydroxyimino-pyrrolidin-1 -yl)-2-oxo-ethyl]-amide, 5-Chloro-1H-indole-2-carboxylic acid [2-(cis-3,4-dihydroxy-pyrrolidin-1 -yl)-2-oxo-ethyl]-amide, 5-Chloro-1H-indole-2-carboxylic acid [2-((3S,4S)-dihydroxy-pyrrolidin-1-yl)-2-oxo-ethyl]-amide, 5-Chloro-1H-indole-2-carboxylic acid [(1S)-benzyl-2-(cis-3,4-dihydroxy-pyrrolidin-1-yl)-2-oxo-ethyl]-amide, 5-Chloro-1H-indole-2-carboxylic acid [2-(1,1-dioxo-thiazolidin-3-yl)-2-oxo-ethyl]-amide, 5-Chloro-1H-indole-2-carboxylic acid (2-oxo-2-thiazolidin-3-yl-ethyl)-amide, 5-Chloro-1H-indole-2-carboxylic acid [(1S)-(4-fluoro-benzyl)-2-(4-hydroxy-piperidin-1-yl)-2-oxo-ethyl]-amide, 5-Chloro-1H-indole-2-carboxylic acid [(1S)-benzyl-2-((3RS)-hydroxy-piperidin-1-yl)-2-oxo-ethyl]-amide, 5-Chloro-1H-indole-2-carboxylic acid [2-oxo-2-((1RS)-oxo-1-thiazolidin-3-yl)-ethyl]-amide, 5-Chloro-1H-indole-2-carboxylic acid [(1S)-(2-fluoro-benzyl)-2-(4-hydroxy-piperidin-1-yl)-2-oxo-ethyl]-amide, 5-Chloro-1H-indole-2-carboxylic acid [(1S)-benzyl-2-((3S,4S)-dihydroxy-pyrrolidin-1-yl)-2-oxo-ethyl]-amide, 5-Chloro-1H-indole-2-carboxylic acid [(1S)-benzyl-2-(3-hydroxy-azetidin-1-yl)-2-oxo-ethyl]-amide, 5-Chloro-1H-indole-2-carboxylic acid [(1 S)-benzyl-2-(3-hydroxyimino-azetidin-1-yl)-2-oxo-ethyl]-amide, 5-Chloro-1H-indole-2-carboxylic acid [(1S)-benzyl-2-(4-hydroxyimino-piperidin-1-yl)-2-oxo-ethyl]-amide, and 5-Chloro-1H-indole-2-carboxylic acid [1-benzyl-2-(3-hydroxypyrrolidin-1-yl)-2-oxo-ethyl]amide.

\* \* \* \* \*